US009925376B2

(12) United States Patent
Hartig et al.

(10) Patent No.: US 9,925,376 B2
(45) Date of Patent: Mar. 27, 2018

(54) TREATMENT OF AUTOIMMUNE DISEASES WITH DEEP BRAIN STIMULATION

(71) Applicant: ALEVA NEUROTHERAPEUTICS, Lausanne (CH)

(72) Inventors: Ingo Hartig, Cuxhaven (DE); Andre Mercanzini, Saint Sulpice (CH); Alain Jordan, Denges (CH); Alexandre Michalis, Le Grand-Saconnex (CH); Marc Boers, Cully (CH); Alain Dransart, Rolle (CH)

(73) Assignee: ALEVA NEUROTHERAPEUTICS, Lausanne (CH)

( * ) Notice: Subject to any disclaimer, the term of this patent is extended or adjusted under 35 U.S.C. 154(b) by 0 days.

(21) Appl. No.: 15/422,393

(22) Filed: Feb. 1, 2017

(65) Prior Publication Data
US 2017/0136238 A1 May 18, 2017

Related U.S. Application Data

(63) Continuation-in-part of application No. 15/281,468, filed on Sep. 30, 2016, which is a continuation of
(Continued)

(51) Int. Cl.
*A61B 6/12* (2006.01)
*A61B 1/05* (2006.01)
(Continued)

(52) U.S. Cl.
CPC .............. *A61N 1/3606* (2013.01); *A61B 5/00* (2013.01); *A61B 5/04001* (2013.01);
(Continued)

(58) Field of Classification Search
CPC ... A61N 1/3606; A61N 1/0531; A61N 1/0534
(Continued)

(56) References Cited

U.S. PATENT DOCUMENTS

| 4,245,645 A | 1/1981 | Arseneault et al. |
| 4,550,733 A | 11/1985 | Liss et al. |

(Continued)

FOREIGN PATENT DOCUMENTS

| EP | 0 677 743 | 10/1995 |
| EP | 0 743 839 | 11/1996 |

(Continued)

OTHER PUBLICATIONS

US 8,388,533, 03/2013, Hafezi et al. (withdrawn)
(Continued)

*Primary Examiner* — Carl H Layno
*Assistant Examiner* — Jon Eric C Morales
(74) *Attorney, Agent, or Firm* — Foley & Lardner LLP; James De Vellis

(57) ABSTRACT

Techniques using electrical stimulation for treating an Autoimmune Disease by means of an implantable pulse generator and at least one electrode. An electrode lead is surgically implanted in a region of the insular cortex to deliver electrical stimulation. The at least one electrode lead and implantable pulse generator contain features that allow the electrical stimulation to be directed to specific volumes of the insular cortex, and ensure that non-therapeutic volumes do not receive electrical stimulation.

20 Claims, 29 Drawing Sheets

Related U.S. Application Data application No. 14/470,423, filed on Aug. 27, 2014, now Pat. No. 9,474,894.

(60) Provisional application No. 62/290,101, filed on Feb. 2, 2016.

(51) Int. Cl.
  *A61B 5/04* (2006.01)
  *A61N 1/05* (2006.01)
  *A61B 5/00* (2006.01)
  *A61N 1/36* (2006.01)
  *H05K 1/11* (2006.01)

(52) U.S. Cl.
  CPC ......... *A61N 1/0531* (2013.01); *A61N 1/0534* (2013.01); *A61N 1/0551* (2013.01); *A61N 1/36139* (2013.01); *A61N 1/36157* (2013.01); *A61N 1/36171* (2013.01); *A61N 1/36175* (2013.01); *A61N 1/36182* (2013.01); *A61N 1/36185* (2013.01); *A61B 6/12* (2013.01); *H05K 1/118* (2013.01)

(58) Field of Classification Search
  USPC .................................................. 600/377, 378
  See application file for complete search history.

(56) References Cited

U.S. PATENT DOCUMENTS

| | | |
|---|---|---|
| 4,837,049 A | 6/1989 | Byers et al. |
| 4,917,093 A | 4/1990 | Dufresne et al. |
| 4,928,297 A | 5/1990 | Tsutsui et al. |
| 4,969,468 A | 11/1990 | Byers et al. |
| 4,989,617 A | 2/1991 | Memberg et al. |
| 5,215,088 A | 6/1993 | Normann et al. |
| 5,345,936 A | 9/1994 | Pomeranz et al. |
| 5,391,250 A | 2/1995 | Cheney et al. |
| 5,400,784 A | 3/1995 | Durand et al. |
| 5,419,777 A | 5/1995 | Hofling |
| 5,496,369 A | 3/1996 | Howard, III |
| 5,524,338 A | 6/1996 | Martyniuk et al. |
| 5,628,317 A | 5/1997 | Starkebaum et al. |
| 5,643,330 A | 7/1997 | Holsheimer et al. |
| 5,679,355 A | 10/1997 | Alexander et al. |
| 5,683,422 A | 11/1997 | Rise |
| 5,697,651 A | 12/1997 | Fernandes |
| 5,697,975 A | 12/1997 | Howard et al. |
| 5,702,429 A | 12/1997 | King |
| 5,713,922 A | 2/1998 | King |
| 5,713,923 A | 2/1998 | Ward et al. |
| 5,716,377 A | 2/1998 | Rise et al. |
| 5,727,552 A | 3/1998 | Ryan |
| 5,752,979 A | 5/1998 | Benabid |
| 5,755,759 A | 5/1998 | Cogan |
| 5,782,798 A | 7/1998 | Rise |
| 5,797,970 A | 8/1998 | Pouvreau |
| 5,800,474 A | 9/1998 | Benabid et al. |
| 5,800,535 A | 9/1998 | Howard, III |
| 5,814,092 A | 9/1998 | King |
| 5,824,029 A | 10/1998 | Weijand et al. |
| 5,792,186 A | 11/1998 | Rise |
| 5,833,709 A | 11/1998 | Rise et al. |
| 5,833,714 A | 11/1998 | Loeb |
| 5,843,148 A | 12/1998 | Gijsbers et al. |
| 5,893,883 A | 4/1999 | Torgerson et al. |
| 5,913,882 A | 6/1999 | King |
| 5,921,924 A | 7/1999 | Avitall |
| 5,927,277 A | 7/1999 | Baudino et al. |
| 5,941,906 A | 8/1999 | Barreras et al. |
| 5,957,958 A | 9/1999 | Schulman et al. |
| 5,975,085 A | 11/1999 | Rise |
| 5,978,702 A | 11/1999 | Ward et al. |
| 5,991,668 A | 11/1999 | Leinders et al. |
| 6,011,996 A | 1/2000 | Gielen et al. |
| 6,018,682 A | 1/2000 | Rise |
| 6,024,095 A | 2/2000 | Stanley, III |
| 6,033,403 A | 3/2000 | Tu et al. |
| 6,038,480 A | 3/2000 | Hrdlicka et al. |
| 6,050,992 A | 4/2000 | Nichols |
| 6,094,598 A | 7/2000 | Elsberry et al. |
| 6,104,960 A | 8/2000 | Duysens et al. |
| 6,109,269 A | 8/2000 | Rise et al. |
| 6,125,300 A | 9/2000 | Weijand et al. |
| 6,128,537 A | 10/2000 | Rise |
| 6,129,685 A | 10/2000 | Howard, III |
| 6,161,047 A | 12/2000 | King et al. |
| 6,205,359 B1 | 3/2001 | Boveja |
| 6,205,361 B1 | 3/2001 | Kuzma et al. |
| 6,216,043 B1 | 4/2001 | Swanson et al. |
| 6,227,203 B1 | 5/2001 | Rise et al. |
| 6,253,109 B1 | 6/2001 | Gielen |
| 6,253,110 B1 | 6/2001 | Brabec et al. |
| 6,263,237 B1 | 7/2001 | Rise |
| 6,266,564 B1 | 7/2001 | Hill et al. |
| 6,295,476 B1 | 9/2001 | Schaenzer |
| 6,319,241 B1 | 11/2001 | King et al. |
| 6,330,466 B1 | 12/2001 | Hofmann et al. |
| 6,337,997 B1 | 1/2002 | Rise |
| 6,343,226 B1 | 1/2002 | Sunde et al. |
| 6,353,762 B1 | 3/2002 | Baudino et al. |
| 6,356,784 B1 | 3/2002 | Lozano et al. |
| 6,356,786 B1 | 3/2002 | Rezai et al. |
| 6,356,787 B1 | 3/2002 | Rezai et al. |
| 6,364,875 B1 | 4/2002 | Stanley, III |
| 6,366,813 B1 | 4/2002 | DiLorenzo |
| 6,374,140 B1 | 4/2002 | Rise |
| 6,375,666 B1 | 4/2002 | Mische |
| 6,379,353 B1 | 4/2002 | Nichols |
| 6,415,187 B1 | 7/2002 | Kuzma et al. |
| 6,434,431 B1 | 8/2002 | Camps et al. |
| 6,479,999 B1 | 11/2002 | DeMeester et al. |
| 6,484,059 B2 | 11/2002 | Gielen |
| 6,493,590 B1 | 12/2002 | Wessman et al. |
| 6,529,774 B1 | 3/2003 | Greene |
| 6,538,443 B2 | 3/2003 | Morich et al. |
| 6,549,812 B1 | 4/2003 | Smits |
| 6,556,873 B1 | 4/2003 | Smits |
| 6,560,472 B2 | 5/2003 | Hill et al. |
| 6,560,486 B1 | 5/2003 | Osorio et al. |
| 6,587,733 B1 | 7/2003 | Cross et al. |
| 6,591,128 B1 | 7/2003 | Wu et al. |
| 6,594,524 B2 | 7/2003 | Esteller et al. |
| 6,597,953 B2 | 7/2003 | Boling |
| 6,643,552 B2 | 11/2003 | Edell et al. |
| 6,671,544 B2 | 12/2003 | Baudino |
| 6,675,046 B2 | 1/2004 | Holsheimer |
| 6,687,538 B1 | 2/2004 | Hrdlicka et al. |
| 6,690,973 B2 | 2/2004 | Hill et al. |
| 6,708,064 B2 | 3/2004 | Rezai |
| 6,718,208 B2 | 4/2004 | Hill et al. |
| 6,718,211 B2 | 4/2004 | Smits |
| 6,741,893 B2 | 5/2004 | Smits |
| 6,745,079 B2 | 6/2004 | King |
| 6,757,970 B1 | 7/2004 | Kuzma et al. |
| 6,795,737 B2 | 9/2004 | Gielen et al. |
| 6,804,552 B2 | 10/2004 | Thompson et al. |
| 6,818,396 B1 | 11/2004 | Bloch et al. |
| 6,829,498 B2 | 12/2004 | Kipke et al. |
| 6,850,802 B2 | 2/2005 | Holsheimer |
| 6,871,098 B2 | 3/2005 | Nuttin et al. |
| 6,882,881 B1 | 4/2005 | Lesser et al. |
| 6,892,097 B2 | 5/2005 | Holsheimer |
| 6,892,438 B1 | 5/2005 | Hill et al. |
| 6,904,306 B1 | 6/2005 | Wu et al. |
| 6,909,920 B2 | 6/2005 | Lokhoff et al. |
| 6,920,359 B2 | 7/2005 | Meadows et al. |
| 6,928,320 B2 | 8/2005 | King |
| 6,950,706 B2 | 9/2005 | Rodriguez et al. |
| 6,950,709 B2 | 9/2005 | Baudino |
| 6,978,171 B2 | 12/2005 | Goetz et al. |
| 6,978,178 B2 | 12/2005 | Sommer et al. |
| 6,999,819 B2 | 2/2006 | Swoyer et al. |
| 7,006,859 B1 | 2/2006 | Osorio et al. |

(56) References Cited

U.S. PATENT DOCUMENTS

| | | |
|---|---|---|
| 7,010,351 B2 | 3/2006 | Firlik et al. |
| 7,010,356 B2 | 3/2006 | Jog et al. |
| 7,024,246 B2 | 4/2006 | Acosta et al. |
| 7,035,690 B2 | 4/2006 | Goetz |
| 7,047,082 B1 | 5/2006 | Schrom et al. |
| 7,047,084 B2 | 5/2006 | Erickson et al. |
| 7,050,856 B2 | 5/2006 | Stypulkowski |
| 7,051,419 B2 | 5/2006 | Schrom et al. |
| 7,061,240 B2 | 6/2006 | Ham et al. |
| 7,063,767 B1 | 6/2006 | Tyson et al. |
| 7,076,292 B2 | 7/2006 | Forsberg |
| 7,077,822 B1 | 7/2006 | Howard, III |
| 7,107,104 B2 | 9/2006 | Keravel et al. |
| 7,133,718 B2 | 11/2006 | Bakken et al. |
| 7,146,222 B2 | 12/2006 | Boling |
| 7,151,961 B1 | 12/2006 | Whitehurst et al. |
| 7,174,219 B2 | 2/2007 | Wahlstrand et al. |
| 7,177,701 B1 | 2/2007 | Pianca |
| 7,181,288 B1 | 2/2007 | Rezai et al. |
| 7,184,829 B2 | 2/2007 | Hill et al. |
| 7,187,978 B2 | 3/2007 | Malek et al. |
| 7,191,016 B2 | 3/2007 | Marshall et al. |
| 7,191,018 B2 | 3/2007 | Gielen et al. |
| 7,200,439 B2 | 4/2007 | Zdeblick et al. |
| 7,203,548 B2 | 4/2007 | Whitehurst et al. |
| 7,204,798 B2 | 4/2007 | Zdeblick et al. |
| 7,204,833 B1 | 4/2007 | Osorio et al. |
| 7,209,787 B2 | 4/2007 | DiLorenzo |
| 7,212,851 B2 | 5/2007 | Donoghue et al. |
| 7,212,867 B2 | 5/2007 | Van Venroo et al. |
| 7,214,189 B2 | 5/2007 | Zdeblick |
| 7,216,000 B2 | 5/2007 | Sieracki et al. |
| 7,216,001 B2 | 5/2007 | Hacker et al. |
| 7,231,256 B2 | 6/2007 | Wahlstrand et al. |
| 7,236,822 B2 | 6/2007 | Dobak, III |
| 7,242,984 B2 | 7/2007 | DiLorenzo |
| 7,276,061 B2 | 10/2007 | Schaer et al. |
| 7,280,867 B2 | 10/2007 | Frei et al. |
| 7,282,030 B2 | 10/2007 | Frei et al. |
| 7,282,050 B2 | 10/2007 | Starkebaum et al. |
| 7,286,878 B2 | 10/2007 | Stypulkowski |
| 7,286,882 B2 | 10/2007 | Cole |
| 7,288,066 B2 | 10/2007 | Drew |
| 7,289,851 B2 | 10/2007 | Gunderson et al. |
| 7,289,852 B2 | 10/2007 | Helfinstine et al. |
| 7,295,880 B2 | 11/2007 | Gielen |
| 7,298,143 B2 | 11/2007 | Jaermann et al. |
| 7,307,223 B2 | 12/2007 | Tyson et al. |
| 7,313,430 B2 | 12/2007 | Urquhart et al. |
| 7,313,440 B2 | 12/2007 | Miesel |
| 7,315,759 B2 | 1/2008 | Markowitz et al. |
| 7,317,947 B2 | 1/2008 | Wahlstrand et al. |
| 7,317,948 B1 | 1/2008 | King et al. |
| 7,319,899 B2 | 1/2008 | Keizer |
| 7,319,904 B2 | 1/2008 | Cross et al. |
| 7,321,798 B2 | 1/2008 | Muhlenberg et al. |
| 7,321,837 B2 | 1/2008 | Osorio et al. |
| 7,322,832 B2 | 1/2008 | Kronich et al. |
| 7,328,057 B2 | 2/2008 | Freas et al. |
| 7,328,068 B2 | 2/2008 | Spinelli et al. |
| 7,328,069 B2 | 2/2008 | Gerber |
| 7,330,760 B2 | 2/2008 | Heruth et al. |
| 7,337,010 B2 | 2/2008 | Howard et al. |
| 7,343,206 B2 | 3/2008 | Sage et al. |
| 7,346,395 B2 | 3/2008 | Lozano et al. |
| 7,356,369 B2 | 4/2008 | Phillips et al. |
| 7,359,837 B2 | 4/2008 | Drew |
| 7,366,572 B2 | 4/2008 | Heruth et al. |
| 7,367,956 B2 | 5/2008 | King |
| 7,369,891 B2 | 5/2008 | Augustijn et al. |
| 7,369,893 B2 | 5/2008 | Gunderson |
| 7,369,894 B2 | 5/2008 | Gerber |
| 7,385,443 B1 | 6/2008 | Denison |
| 7,388,378 B2 | 6/2008 | Gray et al. |
| 7,389,147 B2 | 6/2008 | Wahlstrand et al. |
| 7,390,311 B2 | 6/2008 | Hildebrand et al. |
| 7,391,257 B1 | 6/2008 | Denison et al. |
| 7,392,089 B2 | 6/2008 | Wahlstrand et al. |
| 7,395,113 B2 | 7/2008 | Heruth et al. |
| 7,400,927 B1 | 7/2008 | Litvin |
| 7,406,351 B2 | 7/2008 | Wesselink |
| 7,418,292 B2 | 8/2008 | Shafer |
| 7,421,297 B2 | 9/2008 | Giftakis et al. |
| 7,427,280 B2 | 9/2008 | Gerber |
| 7,429,938 B1 | 9/2008 | Corndorf |
| 7,433,734 B2 | 10/2008 | King |
| 7,442,183 B2 | 10/2008 | Baudino et al. |
| 7,447,545 B2 | 11/2008 | Heruth et al. |
| 7,450,996 B2 | 11/2008 | MacDonald et al. |
| 7,463,917 B2 | 12/2008 | Martinez |
| 7,463,928 B2 | 12/2008 | Lee et al. |
| 7,474,247 B1 | 1/2009 | Heinks et al. |
| 7,479,910 B1 | 1/2009 | Heinks et al. |
| 7,483,748 B2 | 1/2009 | Torgerson et al. |
| 7,489,966 B2 | 2/2009 | Leinders et al. |
| 7,489,970 B2 | 2/2009 | Lee et al. |
| 7,491,181 B2 | 2/2009 | Heruth et al. |
| 7,497,844 B2 | 3/2009 | Spear et al. |
| 7,497,863 B2 | 3/2009 | Solar et al. |
| 7,502,217 B2 | 3/2009 | Zhao et al. |
| 7,505,815 B2 | 3/2009 | Lee et al. |
| 7,505,869 B2 | 3/2009 | Hartlaub |
| 7,515,961 B2 | 4/2009 | Germanson et al. |
| 7,519,431 B2 | 4/2009 | Goetz et al. |
| 7,519,432 B2 | 4/2009 | Bolea et al. |
| 7,520,890 B2 | 4/2009 | Phillips |
| 7,526,339 B2 | 4/2009 | Lahti et al. |
| 7,526,340 B2 | 4/2009 | Drew |
| 7,526,341 B2 | 4/2009 | Goetz et al. |
| 7,529,582 B1 | 5/2009 | DiLorenzo |
| 7,529,586 B2 | 5/2009 | Wahlstrand et al. |
| 7,542,803 B2 | 6/2009 | Heruth et al. |
| 7,546,164 B2 | 6/2009 | King |
| 7,546,166 B2 | 6/2009 | Michels et al. |
| 7,548,775 B2 | 6/2009 | Kipke et al. |
| 7,548,786 B2 | 6/2009 | Lee et al. |
| 7,551,951 B1 | 6/2009 | Osorio et al. |
| 7,551,960 B2 | 6/2009 | Forsberg et al. |
| 7,555,345 B2 | 6/2009 | Wahlstrand et al. |
| 7,561,921 B2 | 7/2009 | Phillips et al. |
| 7,563,141 B2 | 7/2009 | Alexander et al. |
| 7,563,541 B2 | 7/2009 | Howard et al. |
| 7,578,819 B2 | 8/2009 | Bleich et al. |
| 7,580,756 B2 | 8/2009 | Schulte et al. |
| 7,582,387 B2 | 9/2009 | Howard et al. |
| 7,590,451 B2 | 9/2009 | Tronnes et al. |
| 7,590,453 B2 | 9/2009 | Heruth et al. |
| 7,590,455 B2 | 9/2009 | Heruth et al. |
| 7,591,970 B2 | 9/2009 | Olson |
| 7,594,828 B2 | 9/2009 | Alexander et al. |
| 7,594,889 B2 | 9/2009 | St Ores et al. |
| 7,596,399 B2 | 9/2009 | Singhal et al. |
| 7,596,408 B2 | 9/2009 | Singhal et al. |
| 7,596,415 B2 | 9/2009 | Brabec et al. |
| 7,599,730 B2 | 10/2009 | Hunter et al. |
| 7,603,161 B2 | 10/2009 | Wurmfeld et al. |
| 7,603,177 B2 | 10/2009 | Sieracki et al. |
| 7,604,629 B2 | 10/2009 | Gerber et al. |
| 7,604,644 B2 | 10/2009 | Schulte et al. |
| 7,608,458 B2 | 10/2009 | Soykan et al. |
| 7,610,083 B2 | 10/2009 | Drew et al. |
| 7,611,483 B2 | 11/2009 | Gerber et al. |
| 7,614,743 B2 | 11/2009 | Geiger |
| 7,615,015 B2 | 11/2009 | Coleman |
| 7,616,998 B2 | 11/2009 | Nuttin et al. |
| 7,617,002 B2 | 11/2009 | Goetz |
| 7,620,454 B2 | 11/2009 | Dinsmoor et al. |
| 7,622,303 B2 | 11/2009 | Soykan et al. |
| 7,622,988 B2 | 11/2009 | Denison et al. |
| 7,623,053 B2 | 11/2009 | Terry et al. |
| 7,623,918 B2 | 11/2009 | Goetz |
| 7,623,919 B2 | 11/2009 | Goetz et al. |
| 7,623,923 B2 | 11/2009 | Gerber et al. |
| 7,623,930 B2 | 11/2009 | Zeijlemaker et al. |

(56) References Cited

U.S. PATENT DOCUMENTS

| | | |
|---|---|---|
| 7,624,293 B2 | 11/2009 | Osorio et al. |
| 7,628,780 B2 | 12/2009 | Bonner et al. |
| 7,631,415 B2 | 12/2009 | Phillips et al. |
| 7,632,225 B2 | 12/2009 | Stypulkowski |
| 7,635,541 B2 | 12/2009 | Scott et al. |
| 7,637,867 B2 | 12/2009 | Zdeblick |
| 7,640,059 B2 | 12/2009 | Forsberg et al. |
| 7,640,060 B2 | 12/2009 | Zdeblick |
| 7,641,992 B2 | 1/2010 | Howard et al. |
| 7,642,013 B2 | 1/2010 | Howard et al. |
| 7,647,111 B2 | 1/2010 | Ries et al. |
| 7,647,116 B2 | 1/2010 | Bauhahn |
| 7,647,117 B2 | 1/2010 | Bauhahn |
| 7,647,121 B2 | 1/2010 | Wahlstrand et al. |
| 7,650,291 B2 | 1/2010 | Rosenfeld et al. |
| 7,653,433 B2 | 1/2010 | Lozano et al. |
| 7,657,318 B2 | 2/2010 | King et al. |
| 7,657,319 B2 | 2/2010 | Goetz et al. |
| 7,660,620 B2 | 2/2010 | Zeijlemaker et al. |
| 7,660,630 B2 | 2/2010 | Dudding et al. |
| 7,662,140 B2 | 2/2010 | Heruth et al. |
| 7,662,509 B2 | 2/2010 | Howard et al. |
| 7,663,066 B2 | 2/2010 | Tyson et al. |
| 7,664,551 B2 | 2/2010 | Cigaina |
| 7,664,552 B2 | 2/2010 | Wahlstrand et al. |
| 7,668,601 B2 | 2/2010 | Hegland et al. |
| 7,671,594 B2 | 3/2010 | Gray |
| 7,676,271 B2 | 3/2010 | Wahlstrand et al. |
| 7,676,273 B2 | 3/2010 | Goetz et al. |
| 7,676,274 B2 | 3/2010 | Hung et al. |
| 7,680,540 B2 | 3/2010 | Jensen et al. |
| 7,682,355 B2 | 3/2010 | Gerber et al. |
| 7,682,745 B2 | 3/2010 | Howard et al. |
| 7,684,860 B2 | 3/2010 | Wahlstrand et al. |
| 7,684,873 B2 | 3/2010 | Gerber |
| 7,689,289 B2 | 3/2010 | King |
| 7,697,972 B2 | 4/2010 | Verard et al. |
| 7,697,995 B2 | 4/2010 | Cross et al. |
| 7,706,124 B2 | 4/2010 | Zhao et al. |
| 7,706,889 B2 | 4/2010 | Gerber et al. |
| 7,711,421 B2 | 5/2010 | Shafer et al. |
| 7,711,428 B2 | 5/2010 | Janzig et al. |
| 7,711,436 B2 | 5/2010 | Stone |
| 7,713,194 B2 | 5/2010 | Zdeblick |
| 7,713,195 B2 | 5/2010 | Zdeblick |
| 7,720,548 B2 | 5/2010 | King |
| 7,729,768 B2 | 6/2010 | White et al. |
| 7,729,780 B2 | 6/2010 | Vardiman |
| 7,738,958 B2 | 6/2010 | Zdeblick et al. |
| 7,742,823 B2 | 6/2010 | King et al. |
| 7,756,588 B2 | 7/2010 | Jog et al. |
| 7,797,029 B2 | 9/2010 | Gibson et al. |
| 7,822,483 B2 | 10/2010 | Stone et al. |
| 7,853,303 B2 | 12/2010 | Nikumb et al. |
| 7,877,149 B2 | 1/2011 | Zdeblick |
| 7,899,539 B2 | 3/2011 | Whitehurst et al. |
| 7,925,329 B2 | 4/2011 | Zdeblick et al. |
| 7,930,035 B2 | 4/2011 | DiLorenzo |
| 7,935,056 B2 | 5/2011 | Zdeblick |
| 7,941,202 B2 | 5/2011 | Hetke et al. |
| 7,945,336 B2 | 5/2011 | Sauter-Starace et al. |
| 7,969,161 B2 | 6/2011 | Behzadi et al. |
| 7,974,705 B2 | 7/2011 | Zdeblick et al. |
| 7,978,064 B2 | 7/2011 | Zdeblick et al. |
| 7,979,105 B2 | 7/2011 | Kipke et al. |
| 7,983,751 B2 | 7/2011 | Zdeblick et al. |
| 8,000,794 B2 | 8/2011 | Lozano |
| 8,000,808 B2 | 8/2011 | Hegland et al. |
| 8,032,224 B2 | 10/2011 | Miesel et al. |
| 8,036,737 B2 | 10/2011 | Goetz et al. |
| 8,036,743 B2 | 10/2011 | Savage et al. |
| 8,036,748 B2 | 10/2011 | Zdeblick et al. |
| 8,055,334 B2 | 11/2011 | Savage et al. |
| 8,055,353 B2 | 11/2011 | Kreidler et al. |
| 8,099,170 B2 | 1/2012 | Jensen et al. |
| 8,114,021 B2 | 2/2012 | Robertson et al. |
| 8,115,618 B2 | 2/2012 | Robertson et al. |
| 8,121,687 B2 | 2/2012 | Jensen et al. |
| 8,123,684 B2 | 2/2012 | Zdeblick |
| 8,172,762 B2 | 5/2012 | Robertson |
| 8,187,161 B2 | 5/2012 | Li et al. |
| 8,195,308 B2 | 6/2012 | Frank et al. |
| 8,204,586 B2 | 6/2012 | Zdeblick |
| 8,258,962 B2 | 9/2012 | Robertson et al. |
| 8,261,428 B2 | 9/2012 | Fang et al. |
| 8,280,514 B2 | 10/2012 | Lozano et al. |
| 8,332,020 B2 | 12/2012 | Zdeblick |
| 8,355,768 B2 | 1/2013 | Masmanidis et al. |
| 8,412,347 B2 | 4/2013 | Zdeblick |
| 8,473,061 B2 | 6/2013 | Moffitt et al. |
| 8,473,069 B2 | 6/2013 | Bi et al. |
| 8,489,203 B2 | 7/2013 | Ortmann |
| 8,788,064 B2 | 7/2014 | Mercanzini et al. |
| 8,874,232 B2 | 10/2014 | Chen |
| 8,897,891 B2 | 11/2014 | Romero |
| 8,938,308 B2 | 1/2015 | Meadows |
| 9,403,011 B2 | 8/2016 | Mercanzini |
| 9,474,894 B2 | 10/2016 | Mercanzini et al. |
| 2002/0062143 A1 | 5/2002 | Baudino et al. |
| 2003/0004553 A1 | 1/2003 | Grill et al. |
| 2003/0023282 A1 | 1/2003 | Barrett et al. |
| 2003/0036780 A1 | 2/2003 | Barrett et al. |
| 2003/0060822 A1 | 3/2003 | Schaer et al. |
| 2003/0083724 A1 | 5/2003 | Jog et al. |
| 2003/0100823 A1 | 5/2003 | Kipke et al. |
| 2003/0135253 A1 | 7/2003 | Kokones et al. |
| 2003/0176892 A1 | 9/2003 | Shalev |
| 2004/0002635 A1 | 1/2004 | Hargrove et al. |
| 2004/0015205 A1 | 1/2004 | Whitehurst et al. |
| 2004/0039434 A1 | 2/2004 | Schrom et al. |
| 2004/0098074 A1 | 5/2004 | Erickson et al. |
| 2004/0102828 A1 | 5/2004 | Lowry et al. |
| 2004/0122335 A1 | 6/2004 | Sackellares et al. |
| 2004/0133390 A1 | 7/2004 | Osorio et al. |
| 2004/0138517 A1 | 7/2004 | Osorio et al. |
| 2004/0138536 A1 | 7/2004 | Frei et al. |
| 2004/0138720 A1 | 7/2004 | Naisberg et al. |
| 2004/0138722 A1 | 7/2004 | Carroll et al. |
| 2004/0152958 A1 | 8/2004 | Frei et al. |
| 2004/0172089 A1 | 9/2004 | Whitehurst et al. |
| 2004/0193021 A1 | 9/2004 | Zdeblick et al. |
| 2004/0215288 A1 | 10/2004 | Lee et al. |
| 2004/0220637 A1 | 11/2004 | Zdeblick et al. |
| 2004/0225335 A1 | 11/2004 | Whitehurst et al. |
| 2004/0243011 A1 | 12/2004 | Plaza |
| 2004/0249417 A1 | 12/2004 | Ransbury et al. |
| 2004/0254483 A1 | 12/2004 | Zdeblick et al. |
| 2005/0004627 A1 | 1/2005 | Gibson et al. |
| 2005/0008660 A1 | 1/2005 | Kipke et al. |
| 2005/0010261 A1 | 1/2005 | Luders et al. |
| 2005/0021103 A1 | 1/2005 | DiLorenzo |
| 2005/0027284 A1 | 2/2005 | Lozano et al. |
| 2005/0033136 A1 | 2/2005 | Govari et al. |
| 2005/0038489 A1 | 2/2005 | Grill |
| 2005/0049655 A1 | 3/2005 | Boveja et al. |
| 2005/0070971 A1 | 3/2005 | Fowler et al. |
| 2005/0075681 A1 | 4/2005 | Rezai et al. |
| 2005/0113882 A1 | 5/2005 | Cameron et al. |
| 2005/0137647 A1 | 6/2005 | Wallace et al. |
| 2005/0143790 A1 | 6/2005 | Kipke et al. |
| 2005/0154425 A1 | 7/2005 | Boveja et al. |
| 2005/0171558 A1 | 8/2005 | Abovitz et al. |
| 2005/0182455 A1 | 8/2005 | Thrope et al. |
| 2005/0209511 A1 | 9/2005 | Heruth et al. |
| 2005/0209513 A1 | 9/2005 | Heruth et al. |
| 2005/0209643 A1 | 9/2005 | Heruth et al. |
| 2005/0222642 A1 | 10/2005 | Przybyszewski et al. |
| 2005/0240242 A1 | 10/2005 | DiLorenzo |
| 2005/0245988 A1 | 11/2005 | Miesel |
| 2006/0004422 A1 | 1/2006 | De Ridder |
| 2006/0015153 A1 | 1/2006 | Gliner et al. |
| 2006/0030897 A1 | 2/2006 | Gilmer et al. |
| 2006/0041295 A1 | 2/2006 | Osypka |
| 2006/0049957 A1 | 3/2006 | Surgenor et al. |

(56) References Cited

U.S. PATENT DOCUMENTS

| | | |
|---|---|---|
| 2006/0058588 A1 | 3/2006 | Zdeblick |
| 2006/0058727 A1 | 3/2006 | Bernabei |
| 2006/0058855 A1 | 3/2006 | Gill |
| 2006/0095105 A1 | 5/2006 | Jog et al. |
| 2006/0116581 A1 | 6/2006 | Zdeblick et al. |
| 2006/0129203 A1 | 6/2006 | Garabedian et al. |
| 2006/0135877 A1 | 6/2006 | Giftakis et al. |
| 2006/0149336 A1 | 7/2006 | Meadows |
| 2006/0149337 A1 | 7/2006 | John |
| 2006/0149340 A1 | 7/2006 | Karunasiri |
| 2006/0167497 A1 | 7/2006 | Armstrong et al. |
| 2006/0173263 A1 | 8/2006 | He et al. |
| 2006/0173510 A1 | 8/2006 | Besio et al. |
| 2006/0178709 A1 | 8/2006 | Foster et al. |
| 2006/0195154 A1 | 8/2006 | Jaax et al. |
| 2006/0200206 A1 | 9/2006 | Firlik et al. |
| 2006/0212090 A1 | 9/2006 | Lozano et al. |
| 2006/0241717 A1 | 10/2006 | Whitehurst et al. |
| 2006/0258951 A1 | 11/2006 | Bleich et al. |
| 2006/0264777 A1 | 11/2006 | Drew |
| 2006/0265022 A1 | 11/2006 | John et al. |
| 2006/0276866 A1 | 12/2006 | McCreery |
| 2006/0282014 A1 | 12/2006 | Kipke et al. |
| 2006/0293720 A1 | 12/2006 | DiLorenzo |
| 2006/0293721 A1 | 12/2006 | Tarver et al. |
| 2007/0027498 A1 | 2/2007 | Maschino et al. |
| 2007/0027500 A1 | 2/2007 | Maschino et al. |
| 2007/0027514 A1 | 2/2007 | Gerber |
| 2007/0043268 A1 | 2/2007 | Russell |
| 2007/0060974 A1 | 3/2007 | Lozano |
| 2007/0067002 A1 | 3/2007 | Lozano |
| 2007/0067003 A1 | 3/2007 | Sanchez et al. |
| 2007/0088403 A1 | 4/2007 | Wyler et al. |
| 2007/0088404 A1 | 4/2007 | Wyler et al. |
| 2007/0093870 A1 | 4/2007 | Maschino |
| 2007/0100389 A1 | 5/2007 | Jaax et al. |
| 2007/0100392 A1 | 5/2007 | Maschino et al. |
| 2007/0100393 A1 | 5/2007 | Whitehurst et al. |
| 2007/0100398 A1 | 5/2007 | Sloan |
| 2007/0106143 A1 | 5/2007 | Flaherty |
| 2007/0123765 A1 | 5/2007 | Hetke et al. |
| 2007/0123944 A1 | 5/2007 | Zdeblick |
| 2007/0135721 A1 | 6/2007 | Zdeblick |
| 2007/0142872 A1 | 6/2007 | Mickle et al. |
| 2007/0150024 A1 | 6/2007 | Leyde et al. |
| 2007/0173890 A1 | 7/2007 | Armstrong |
| 2007/0173896 A1 | 7/2007 | Zdeblick |
| 2007/0173897 A1 | 7/2007 | Zdeblick |
| 2007/0173901 A1 | 7/2007 | Reeve |
| 2007/0173908 A1 | 7/2007 | Begnaud |
| 2007/0179558 A1 | 8/2007 | Gliner et al. |
| 2007/0179569 A1 | 8/2007 | Zdeblick |
| 2007/0185537 A1 | 8/2007 | Zdeblick |
| 2007/0185544 A1 | 8/2007 | Dawant et al. |
| 2007/0185548 A1 | 8/2007 | Zdeblick |
| 2007/0185549 A1 | 8/2007 | Zdeblick |
| 2007/0197892 A1 | 8/2007 | Shen et al. |
| 2007/0203537 A1 | 8/2007 | Goetz et al. |
| 2007/0203546 A1 | 8/2007 | Stone et al. |
| 2007/0208394 A1 | 9/2007 | King et al. |
| 2007/0213784 A1 | 9/2007 | Pless |
| 2007/0213785 A1 | 9/2007 | Osorio et al. |
| 2007/0213786 A1 | 9/2007 | Sackellares et al. |
| 2007/0219591 A1 | 9/2007 | Zdeblick et al. |
| 2007/0225674 A1 | 9/2007 | Molnar et al. |
| 2007/0225773 A1 | 9/2007 | Shen et al. |
| 2007/0225774 A1 | 9/2007 | Eskandar et al. |
| 2007/0233192 A1 | 10/2007 | Craig |
| 2007/0249953 A1 | 10/2007 | Frei et al. |
| 2007/0249954 A1 | 10/2007 | Virag et al. |
| 2007/0250133 A1 | 10/2007 | Carlson et al. |
| 2007/0255323 A1 | 11/2007 | Werder et al. |
| 2007/0255338 A1 | 11/2007 | Wahlstrand |
| 2007/0255374 A1 | 11/2007 | Kolafa et al. |
| 2007/0255531 A1 | 11/2007 | Drew |
| 2007/0265683 A1 | 11/2007 | Ehrlich |
| 2007/0282389 A1 | 12/2007 | Moxon et al. |
| 2007/0293908 A1 | 12/2007 | Cowan et al. |
| 2008/0021514 A1 | 1/2008 | Pless |
| 2008/0021517 A1 | 1/2008 | Dietrich |
| 2008/0027289 A1 | 1/2008 | Zdeblick |
| 2008/0027487 A1 | 1/2008 | Patel et al. |
| 2008/0027503 A1 | 1/2008 | Marrosu et al. |
| 2008/0027504 A1 | 1/2008 | Bedenbaugh |
| 2008/0027540 A1 | 1/2008 | Cumming |
| 2008/0039895 A1 | 2/2008 | Fowler et al. |
| 2008/0046012 A1 | 2/2008 | Covalin et al. |
| 2008/0046013 A1 | 2/2008 | Lozano |
| 2008/0058630 A1 | 3/2008 | Robertson |
| 2008/0077186 A1 | 3/2008 | Thompson et al. |
| 2008/0077191 A1 | 3/2008 | Morrell |
| 2008/0103547 A1 | 5/2008 | Okun et al. |
| 2008/0103548 A1 | 5/2008 | Fowler et al. |
| 2008/0103578 A1 | 5/2008 | Gerber |
| 2008/0114417 A1 | 5/2008 | Leyde |
| 2008/0119900 A1 | 5/2008 | DiLorenzo |
| 2008/0139870 A1 | 6/2008 | Gliner et al. |
| 2008/0140152 A1 | 6/2008 | Imran et al. |
| 2008/0154328 A1 | 6/2008 | Thompson et al. |
| 2008/0154331 A1 | 6/2008 | John et al. |
| 2008/0161881 A1 | 7/2008 | Firlik et al. |
| 2008/0161896 A1 | 7/2008 | Sauter-Starace et al. |
| 2008/0172103 A1 | 7/2008 | Kao et al. |
| 2008/0177196 A1 | 7/2008 | Burdick et al. |
| 2008/0188905 A1 | 8/2008 | Swartz |
| 2008/0195166 A1 | 8/2008 | Sun et al. |
| 2008/0195227 A1 | 8/2008 | Boling et al. |
| 2008/0208283 A1 | 8/2008 | Vetter et al. |
| 2008/0208287 A1 | 8/2008 | Palermo et al. |
| 2008/0215125 A1 | 9/2008 | Farah et al. |
| 2008/0221642 A1 | 9/2008 | Humayun et al. |
| 2008/0242976 A1 | 10/2008 | Robertson et al. |
| 2008/0255439 A1 | 10/2008 | Tang et al. |
| 2008/0255629 A1 | 10/2008 | Jenson et al. |
| 2008/0255647 A1 | 10/2008 | Jensen et al. |
| 2008/0269835 A1 | 10/2008 | Carlson et al. |
| 2008/0269842 A1 | 10/2008 | Giftakis et al. |
| 2008/0269854 A1 | 10/2008 | Hegland et al. |
| 2008/0275526 A1 | 11/2008 | Lozano |
| 2008/0284599 A1 | 11/2008 | Zdeblick et al. |
| 2008/0294218 A1 | 11/2008 | Savage et al. |
| 2008/0300652 A1 | 12/2008 | Lim et al. |
| 2008/0306394 A1 | 12/2008 | Zdeblick et al. |
| 2008/0312726 A1 | 12/2008 | Frank et al. |
| 2008/0316020 A1 | 12/2008 | Robertson et al. |
| 2009/0027504 A1 | 1/2009 | Lim et al. |
| 2009/0062879 A1 | 3/2009 | Li et al. |
| 2009/0082645 A1 | 3/2009 | Hafezi et al. |
| 2009/0105784 A1 | 4/2009 | Massoud-Ansari et al. |
| 2009/0118806 A1 | 5/2009 | Vetter et al. |
| 2009/0132042 A1 | 5/2009 | Hetke et al. |
| 2009/0171416 A1 | 7/2009 | Firlik et al. |
| 2009/0177144 A1 | 7/2009 | Masmanidis et al. |
| 2009/0187196 A1 | 7/2009 | Vetter |
| 2009/0204183 A1 | 8/2009 | Kreidler et al. |
| 2009/0240314 A1 | 9/2009 | Kong et al. |
| 2009/0253977 A1 | 10/2009 | Kipke et al. |
| 2009/0256702 A1 | 10/2009 | Robertson et al. |
| 2009/0292325 A1 | 11/2009 | Cederna et al. |
| 2009/0299174 A1 | 12/2009 | Wright et al. |
| 2009/0306728 A1 | 12/2009 | Wright et al. |
| 2009/0306729 A1 | 12/2009 | Doerr |
| 2009/0312770 A1 | 12/2009 | Kozai et al. |
| 2009/0318824 A1 | 12/2009 | Nishida et al. |
| 2009/0325424 A1 | 12/2009 | Aarts et al. |
| 2010/0014541 A1 | 1/2010 | Harriman |
| 2010/0015274 A1 | 1/2010 | Fill |
| 2010/0030298 A1 | 2/2010 | Martens et al. |
| 2010/0036468 A1 | 2/2010 | Decre et al. |
| 2010/0069717 A1 | 3/2010 | Hafezi et al. |
| 2010/0076536 A1 | 3/2010 | Merz et al. |
| 2010/0087853 A1 | 4/2010 | Kipke et al. |
| 2010/0100152 A1 | 4/2010 | Martens et al. |
| 2010/0106178 A1 | 4/2010 | Obermiller et al. |

(56) References Cited

U.S. PATENT DOCUMENTS

| | | |
|---|---|---|
| 2010/0114193 A1 | 5/2010 | Lozano et al. |
| 2010/0114234 A1 | 5/2010 | Zdeblick |
| 2010/0114250 A1 | 5/2010 | Zdeblick |
| 2010/0130844 A1 | 5/2010 | Williams et al. |
| 2010/0145216 A1 | 6/2010 | He et al. |
| 2010/0145414 A1 | 6/2010 | Decre et al. |
| 2010/0152747 A1 | 6/2010 | Padiy et al. |
| 2010/0198315 A1 | 8/2010 | Martens et al. |
| 2010/0249883 A1 | 9/2010 | Zdeblick |
| 2010/0274305 A1 | 10/2010 | Gliner et al. |
| 2010/0292602 A1 | 11/2010 | Worrell et al. |
| 2010/0298908 A1 | 11/2010 | Vardiman |
| 2010/0298917 A1 | 11/2010 | Vardiman |
| 2010/0298918 A1 | 11/2010 | Vardiman |
| 2010/0312188 A1 | 12/2010 | Robertson et al. |
| 2010/0312228 A1 | 12/2010 | Zdeblick et al. |
| 2010/0318163 A1 | 12/2010 | Zdeblick |
| 2010/0331807 A1 | 12/2010 | Whitehurst et al. |
| 2011/0001488 A1 | 1/2011 | Behzadi et al. |
| 2011/0022124 A1 | 1/2011 | Zdeblick et al. |
| 2011/0034964 A1 | 2/2011 | Bi et al. |
| 2011/0034970 A1 | 2/2011 | Barker |
| 2011/0040203 A1 | 2/2011 | Savage et al. |
| 2011/0071766 A1 | 3/2011 | Dolan et al. |
| 2011/0130809 A1 | 6/2011 | Zdeblick |
| 2011/0152988 A1 | 6/2011 | Whitehurst et al. |
| 2011/0154655 A1 | 6/2011 | Hetke et al. |
| 2011/0184495 A1 | 7/2011 | Wang et al. |
| 2011/0190860 A1 | 8/2011 | Harberts et al. |
| 2011/0196454 A1 | 8/2011 | Strand et al. |
| 2011/0208225 A1 | 8/2011 | Martens et al. |
| 2011/0213382 A1 | 9/2011 | Decre et al. |
| 2011/0218417 A1 | 9/2011 | Boogaard et al. |
| 2011/0224757 A1 | 9/2011 | Zdeblick et al. |
| 2011/0224765 A1 | 9/2011 | Harberts et al. |
| 2011/0224766 A1 | 9/2011 | Tol et al. |
| 2011/0282179 A1 | 11/2011 | Zdeblick |
| 2011/0301665 A1 | 12/2011 | Mercanzini et al. |
| 2012/0004520 A1 | 1/2012 | Whitworth et al. |
| 2012/0004527 A1 | 1/2012 | Thompson et al. |
| 2012/0004716 A1 | 1/2012 | Langhammer et al. |
| 2012/0007734 A1 | 1/2012 | Berkman et al. |
| 2012/0022341 A1 | 1/2012 | Zdeblick |
| 2012/0035684 A1 | 2/2012 | Thompson et al. |
| 2012/0053344 A1 | 3/2012 | Lagos Gonzalez |
| 2012/0059444 A1 | 3/2012 | Pardoel et al. |
| 2012/0062379 A1 | 3/2012 | Hafezi et al. |
| 2012/0095355 A1 | 4/2012 | Zdeblick |
| 2012/0109262 A1 | 5/2012 | Martens |
| 2012/0109599 A1 | 5/2012 | Martens |
| 2012/0116188 A1 | 5/2012 | Frank et al. |
| 2012/0136420 A1 | 5/2012 | Pardoel et al. |
| 2012/0150256 A1 | 6/2012 | Martens |
| 2012/0184837 A1 | 7/2012 | Martens et al. |
| 2012/0253442 A1 | 10/2012 | Gliner et al. |
| 2012/0277821 A1 | 11/2012 | Martens et al. |
| 2012/0296444 A1 | 11/2012 | Greenberg et al. |
| 2012/0303088 A1 | 11/2012 | Van Kaam et al. |
| 2012/0303089 A1 | 11/2012 | Martens et al. |
| 2012/0303107 A1 | 11/2012 | Decre et al. |
| 2012/0316630 A1 | 12/2012 | Firlik et al. |
| 2013/0009691 A1 | 1/2013 | Blanken et al. |
| 2013/0030366 A1 | 1/2013 | Robertson et al. |
| 2013/0046356 A1 | 2/2013 | Jensen et al. |
| 2013/0060102 A1 | 3/2013 | Zdeblick |
| 2013/0085361 A1* | 4/2013 | Mercanzini ........ A61B 5/04001 600/377 |
| 2013/0131754 A1 | 5/2013 | Sarvazyan |
| 2013/0144132 A1 | 6/2013 | Hafezi et al. |
| 2013/0172716 A1 | 7/2013 | Lozano et al. |
| 2013/0193950 A1 | 8/2013 | Hafezi et al. |
| 2013/0204318 A1 | 8/2013 | Young |
| 2013/0223028 A1 | 8/2013 | Arne et al. |
| 2013/0231188 A1 | 9/2013 | Berberich et al. |
| 2013/0282090 A1 | 10/2013 | Decre et al. |
| 2013/0345780 A1 | 12/2013 | Tabada et al. |
| 2013/0345789 A1 | 12/2013 | Havel et al. |
| 2014/0039578 A1 | 2/2014 | Whitehurst et al. |

FOREIGN PATENT DOCUMENTS

| | | |
|---|---|---|
| EP | 0 892 654 | 1/1999 |
| EP | 0 895 483 | 2/1999 |
| EP | 0 959 942 | 12/1999 |
| EP | 1 048 319 | 11/2000 |
| EP | 1 062 973 | 12/2000 |
| EP | 1 102 607 | 5/2001 |
| EP | 1 257 320 | 11/2002 |
| EP | 1 446 189 | 8/2004 |
| EP | 1 514 576 | 3/2005 |
| EP | 1 750 798 | 2/2007 |
| EP | 1 890 764 | 2/2008 |
| EP | 1 931 419 | 6/2008 |
| EP | 1 985 579 | 10/2008 |
| EP | 1 993 665 | 11/2008 |
| EP | 2 046 441 | 4/2009 |
| EP | 2 066 396 B1 | 6/2009 |
| EP | 2 069 003 | 6/2009 |
| EP | 2 131 916 | 12/2009 |
| EP | 2 167 188 | 3/2010 |
| EP | 2 320 221 | 5/2011 |
| EP | 2 341 979 | 7/2011 |
| EP | 2 456 513 A1 | 5/2012 |
| EP | 2 542 303 A1 | 1/2013 |
| EP | 2 559 454 A1 | 2/2013 |
| EP | 2 604 313 | 6/2013 |
| EP | 2 620 179 A1 | 7/2013 |
| EP | 2 623 154 A1 | 8/2013 |
| EP | 2 626 108 A1 | 8/2013 |
| EP | 2 626 109 A1 | 8/2013 |
| EP | 2 626 110 A1 | 8/2013 |
| EP | 2 626 111 A1 | 8/2013 |
| EP | 2 656 875 A1 | 10/2013 |
| EP | 2 656 876 A1 | 10/2013 |
| EP | 2 674 193 A1 | 12/2013 |
| WO | WO-98/10010 | 3/1998 |
| WO | WO-02/068042 | 9/2002 |
| WO | WO-03/022354 | 3/2003 |
| WO | WO-03/028521 | 4/2003 |
| WO | WO-03/066152 | 8/2003 |
| WO | WO-03/066153 A2 | 8/2003 |
| WO | WO-03/066157 | 8/2003 |
| WO | WO-2004/045707 | 6/2004 |
| WO | WO-2005/002467 | 1/2005 |
| WO | WO-2005/067792 | 7/2005 |
| WO | WO-2005/112216 | 11/2005 |
| WO | WO-2006/029257 | 3/2006 |
| WO | WO-2006/047265 | 5/2006 |
| WO | WO-2006/104432 | 10/2006 |
| WO | WO-2007/002144 | 1/2007 |
| WO | WO-2007/009070 | 1/2007 |
| WO | WO-2007/011611 | 1/2007 |
| WO | WO-2007/025356 | 3/2007 |
| WO | WO-2007/028003 A2 | 3/2007 |
| WO | WO-2007/042999 | 4/2007 |
| WO | WO-2007/092330 | 8/2007 |
| WO | WO-2007/100428 | 9/2007 |
| WO | WO-2007/108718 | 9/2007 |
| WO | WO-2008/003318 | 1/2008 |
| WO | WO-2008/005478 | 1/2008 |
| WO | WO-2008/016881 | 2/2008 |
| WO | WO-2008/035285 | 3/2008 |
| WO | WO-2008/035344 | 3/2008 |
| WO | WO-2008/051463 | 5/2008 |
| WO | WO-2008/064269 A2 | 5/2008 |
| WO | WO-2008/068759 | 6/2008 |
| WO | WO-2008/075294 | 6/2008 |
| WO | WO-2008/077440 | 7/2008 |
| WO | WO-2008/089726 | 7/2008 |
| WO | WO-2008/107822 | 9/2008 |
| WO | WO-2008/109298 | 9/2008 |
| WO | WO-2008/133616 | 11/2008 |
| WO | WO-2008/133683 | 11/2008 |
| WO | WO-2008/138305 | 11/2008 |

(56) References Cited

FOREIGN PATENT DOCUMENTS

| WO | WO-2010/014686 | 2/2010 |
|---|---|---|
| WO | WO-2010/055421 | 5/2010 |
| WO | WO-2011/115999 | 9/2011 |
| WO | WO-2013/014206 | 1/2013 |
| WO | WO-2016/030823 | 3/2016 |

OTHER PUBLICATIONS

US 8,469,885, 06/2013, Hafezi et al. (withdrawn)
U.S. Appl. No. 07/151,961, filed Feb. 3, 1988, Masahiko Okunuki et al.
Australian Patent Examination Report No. 1 dated Jan. 30, 2014 in corresponding Australian Application No. 2010326613, 2 pages.
Australian Patent Examination Report No. 1 dated Jan. 31, 2014 in corresponding Australian Application No. 2009315316, 3 pages.
Benabid, et al. "Combined (Thalamotomy and Stimulation) Stereotactic Surgery of the VIM Thalamic Nucleus for Bilateral Parkinson Disease", Proceedings of the Meeting of the American Society for Stereotactic and Functional Neurosurgery, Montreal 1987 Appl. Neurophysiol. 50: 344-346.
CA Office Action in CA Application No. 2795159 dated Jan. 27, 2017 (4 pages).
CA Office Action on CA Appln. No. 2782710 dated Aug. 14, 2017 (5 pages).
Canadian Office Action for Application No. 2,743,575 dated Sep. 25, 2014, 3 pages.
Cogan, S., et al. "Plasma-enhanced chemical vapor deposited silicon carbide as an implantable dielectric coating." Journal of Biomedical Materials Research Part A 67.3 (2003): 856-867.
Communication from the European Patent Office in Application No. 09795810.2 dated Sep. 14, 2011.
Decision of Rejection and Decision for Dismissal of Amendment in JP Patent Application No. 2011543841 dated May 15, 2014.
Decision of Rejection for Japanese Appl. Ser. No. 2012-541491 dated Oct. 26, 2015.
EIC Biomedical, "Thin-film Encapsulation for Neural Recording and Stimulation Electrodes", Silicon carbide and oxycarbide, Apr. 2008: pp. 1-2.
English translation of Notice of Reasons for Rejection in JP application No. 2011-543841 dated Oct. 21, 2013.
European Communication and Search Report for Application No. 09795810.2 dated Sep. 25, 2013.
European Communication dated May 22, 2013 including search report for EP application No. 12198290.4-1652.
European Search Report for Appl. Ser. No. 09803534.8 dated Jul. 21, 2011.
European Search Report for Appl. Ser. No. 13169272.5 dated Aug. 30, 2013.
European Search Report for application No. EP 14172592 dated Aug. 28, 2014, 8 pages.
Examination Report for EP09795810.2 dated Jun. 22, 2012.
Examination Report from European Patent Office in 09 795 810.2 dated May 8, 2014.
Examination Report in AU Patent Application No. 2009276603 dated Mar. 3, 2014.
Examination report in AU Patent Application No. 2011234422 dated Feb. 11, 2014.
Examination Report in EP Patent Application No. 11 711 884.4 dated Mar. 28, 2014.
Extended European Search Report on EP Appln. No. 16199868.7 dated Apr. 28, 2017 (7 pages).
Fierce Medical Devices, "Medtronic Announces First U.S. Implant of World's Smallest, Minimally Invasive Cardiac Pacemaker", Feb. 20, 2014, pp. 1-3.
Gibney, "St. Jude places its Nanostim leadless pacemaker in a U.K. patient", Fierce Medical Devices, Jan. 27, 2014, pp. 1-3.
International Preliminary Report on Patentability for PCT/EP2010/ 068658 dated Jun. 5, 2012.
International Preliminary Report on Patentability for PCT/IB2009/ 007715 dated May 17, 2011.
International Preliminary Report on Patentability for PCT/IB2015/ 056437 dated Mar. 9, 2017.
International Preliminary Report on Patentability for PCT/IB2015/ 056438 dated Mar. 9, 2017.
International Preliminary Report on Patentability for PCT/US2009/ 052077 dated Feb. 1, 2011.
International Search Report and Written Opinion for PCT Appl. Ser. No. PCT/IB2015/053610 dated Jul. 20, 2015.
International Search Report and Written Opinion for PCT Appl. Ser. No. PCT/IB2015/056437 dated Nov. 5, 2015.
International Search Report and Written Opinion for PCT Appl. Ser. No. PCT/IB2015/056438 dated Nov. 5, 2015.
International Search Report and Written Opinion for PCT/EP2010/ 068658 dated Mar. 21, 2011.
International Search Report and Written Opinion for PCT/IB2017/ 050551 dated Mar. 29, 2017.
International Search Report and Written Opinion in Application No. PCT/EP2011/055045 dated Jul. 18, 2011.
International Search Report and Written Opinion in PCT/US09/ 52077 dated Sep. 25, 2009.
International Search Report for PCT/IB2009/007715 dated Apr. 22, 2010.
Notice of Allowance for U.S. Appl. No. 14/287,917 dated Apr. 15, 2015.
Notice of Allowance on U.S. Appl. No. 14/470,423 dated Jun. 15, 2016.
Notice of Allowance on U.S. Appl. No. 14/945,952 dated Dec. 7, 2016.
Notice of Allowance on U.S. Appl. No. 15/194,033 dated Oct. 27, 2016.
Notice of Reasons for Rejection for Japanese Patent Application No. 2011-543841 dated May 30, 2013.
Notice of Reasons for Rejection in JP Patent Application No. 2011-521276 dated Mar. 3, 2014.
Notice of Reasons for Rejection in JP Patent Application No. 2011-521276 dated May 30, 2013.
Notice of Reasons for Rejections for Japanese Patent Appl. Ser. No. 2012-541491 dated Aug. 28, 2014, 8 pages.
Office Action for CA 2,732,309 dated Nov. 8, 2016.
Office Action for CA 2,782,710 dated Oct. 19, 2016.
Office Action for Canadian Appl. Ser. No. 2732309 dated Dec. 7, 2015.
Office Action for Canadian Appl. Ser. No. 2743575 dated Jan. 21, 2015 (4 pages).
Office Action for Canadian Appl. Ser. No. 2743575 dated Jun. 11, 2015.
Office Action for Canadian Appl. Ser. No. 2743575 dated Sep. 14, 2015.
Office Action for EPO Appl. Ser. No. 10787404.2 dated May 6, 2015.
Office Action for EPO Appl. Ser. No. 14172592.9 dated Aug. 20, 2015.
Office Action for European Application No. 10787404.2 dated Mar. 26, 2013.
Office Action for Japanese Appl. Ser. No. 2013-501857 dated Jun. 1, 2015.
Office Action for Japanese Appl. Ser. No. 2013-501857 dated Sep. 17, 2014.
Office Action on U.S. Appl. No. 14/731,296 dated Oct. 5, 2016.
Office Action on U.S. Appl. No. 14/945,952 dated Jul. 26, 2016.
Office Action on U.S. Appl. No. 15/194,033 dated Aug. 22, 2016.
Office Action on U.S. Appl. No. 15/281,468 dated Dec. 7, 2016.
Pollak, et al. "Effets de la Stimulation du Noyau Sous-Thalamique Dans La Maladie De Parkinson", Rev. Neurol (Paris),149, 3, 175-176. Mason, Paris, 1993.
Rousche, et al., "Flexible polyimide-based intracortical electrode arrays with bioactive capability," IEEE Transactions on Biomedical Engineering 48(3): 361-371 (Mar. 2001).
Search Report for EP 16190439.6 dated Jul. 27, 2017.
Second Notice of Reasons for Rejection for Japanese Application No. 2012-541491 dated Apr. 8, 2015.

(56) References Cited

OTHER PUBLICATIONS

Sepulveda et al., "Finite Element Analysis of Current Pathways with Implanted Electrodes", J. Biomed. Eng. 1983, vol. 5, pp. 41-48.
U.S. Corrected Notice of Allowability for U.S. Appl. No. 14/470,356 dated May 18, 2016.
U.S. Notice of Allowance for U.S. Appl. No. 14/287,917 dated Jul. 20, 2015.
U.S. Notice of Allowance for U.S. Appl. No. 14/309,491 dated May 11, 2016.
U.S. Notice of Allowance for U.S. Appl. No. 14/316,154 dated Apr. 20, 2015.
U.S. Notice of Allowance for U.S. Appl. No. 14/470,356 dated Apr. 13, 2016.
U.S. Notice of Allowance for U.S. Appl. No. 14/470,356 dated Mar. 18, 2016.
U.S. Notice of Allowance for U.S. Appl. No. 13/512,936 dated Feb. 20, 2014.
U.S. Notice of Allowance for U.S. Appl. No. 13/512,936 dated Nov. 25, 2013.
U.S. Notice of Allowance for U.S. Appl. No. 13/056,261 dated May 8, 2014.
U.S. Notice of Allowance in U.S. Appl. No. 13/128,821 dated Dec. 24, 2013.
U.S. Notice of Allowance in U.S. Appl. No. 13/128,821 dated Mar. 25, 2014.
U.S. Notice of Allowance on U.S. Appl. No. 13/638,435 dated Sep. 16, 2016.
U.S. Office Action for U.S. Appl. No. 13/128,821 dated Nov. 14, 2013.
U.S. Office Action for U.S. Appl. No. 13/638,435 dated Feb. 10, 2016.
U.S. Office Action for U.S. Appl. No. 13/638,435 dated Jun. 30, 2015.
U.S. Office Action for U.S. Appl. No. 13/638,435 dated Mar. 12, 2015.
U.S. Office Action for U.S. Appl. No. 14/309,491 dated Jul. 28, 2015.
U.S. Office Action for U.S. Appl. No. 14/309,491 dated Mar. 3, 2016.
U.S. Office Action for U.S. Appl. No. 14/470,423 dated Jan. 21, 2016.
U.S. Office Action for U.S. Appl. No. 13/128,821 dated Dec. 14, 2012.
U.S. Office Action for U.S. Appl. No. 13/128,821 dated Apr. 24, 2012.
U.S. Office Action for U.S. Appl. No. 14/316,154 dated Dec. 18, 2014.
U.S. Office Action for U.S. Appl. No. 13/512,936 dated Aug. 14, 2013.
U.S. Office Action for U.S. Appl. No. 13/056,261 dated Jan. 9, 2014.
U.S. Office Action in U.S. Appl. No. 13/056,261 dated Aug. 7, 2013.
U.S. Office Action on U.S. Appl. No. 14/287,917 dated Sep. 26, 2014.
U.S. Office Action on U.S. Appl. No. 14/731,296 dated Apr. 6, 2017.
U.S. Office Action on U.S. Appl. No. 15/281,468 dated Jun. 14, 2017.
U.S. Office Action on U.S. Appl. No. 15/369,766 dated Apr. 20, 2017.
U.S. Office Action on U.S. Appl. No. 15/426,816 dated Mar. 21, 2017.
Written Opinion for PCT/EP2010/068658 dated Jun. 1, 2012.
Written Opinion for Singapore Application No. 201103393-3 dated May 2, 2012.
Written Opinion of the International Search Authority for PCT/IB2009/07715 dated May 12, 2011.

\* cited by examiner

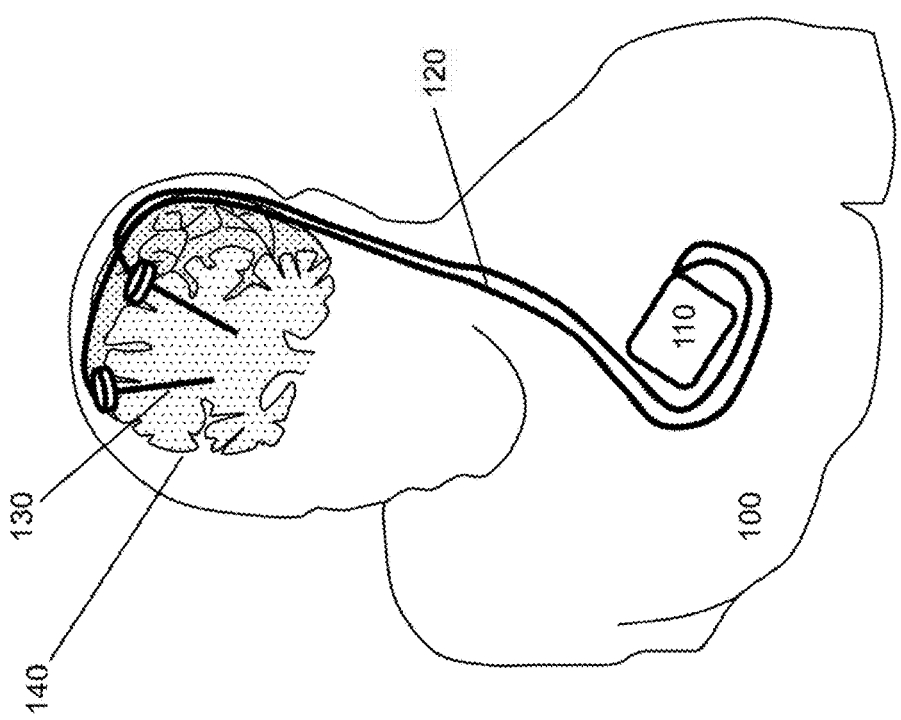

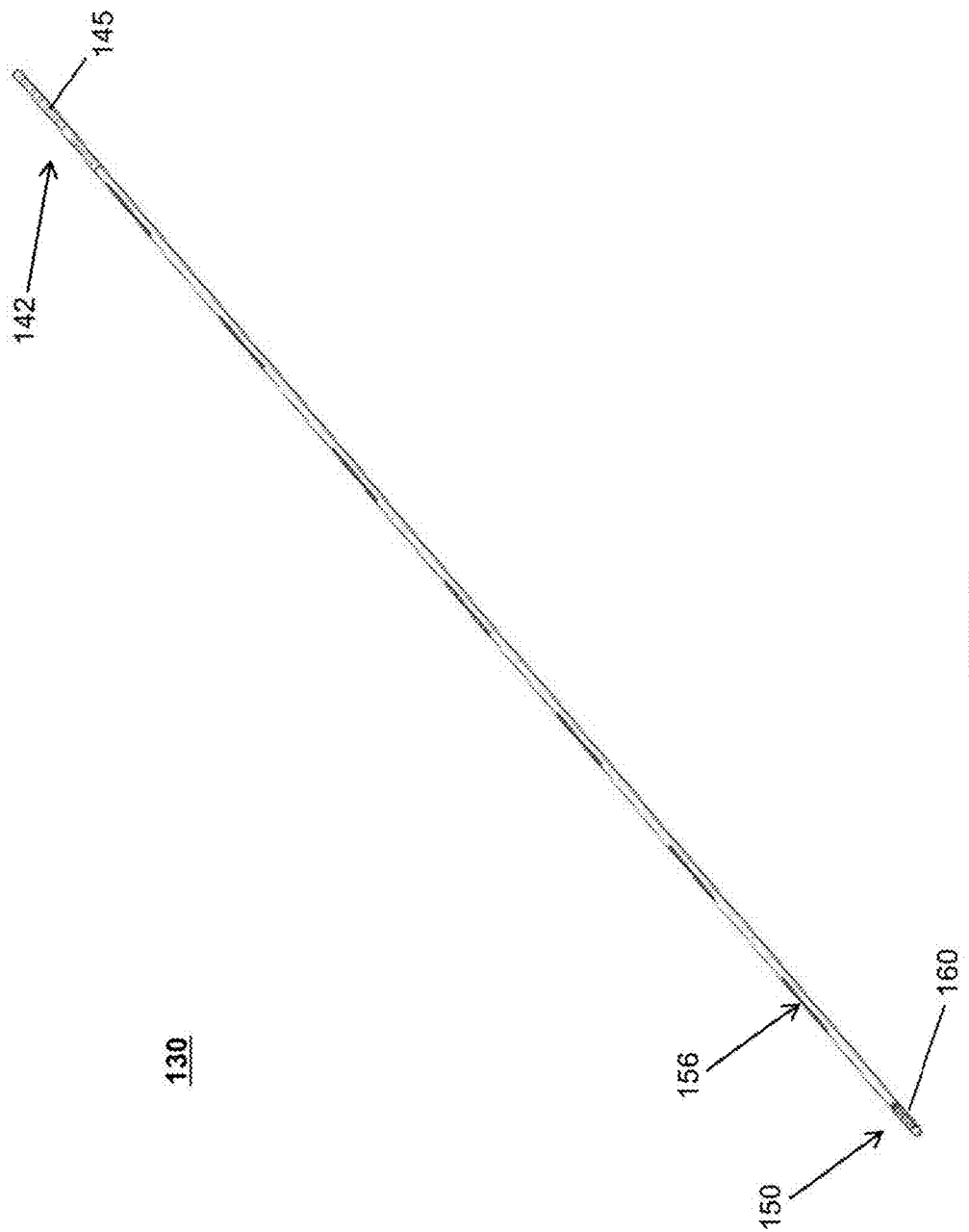

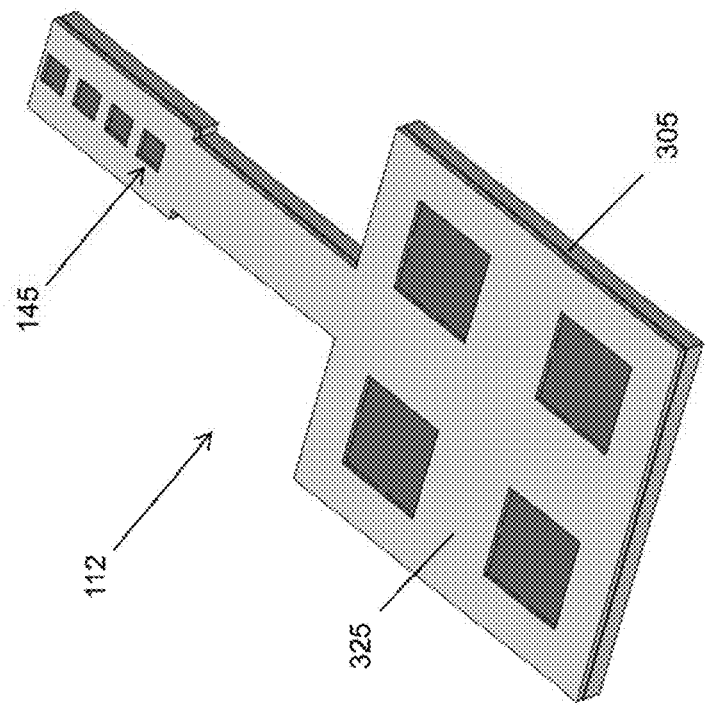
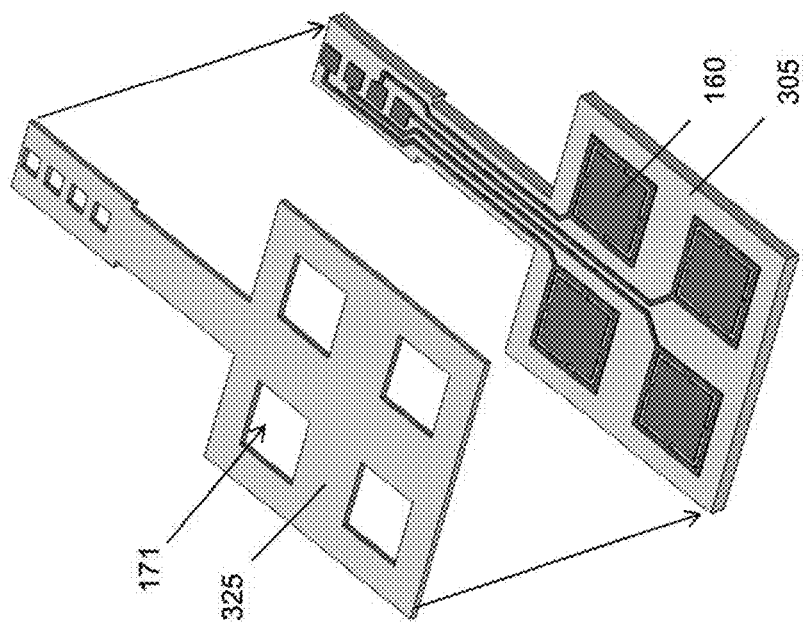
FIG. 4E
FIG. 4D

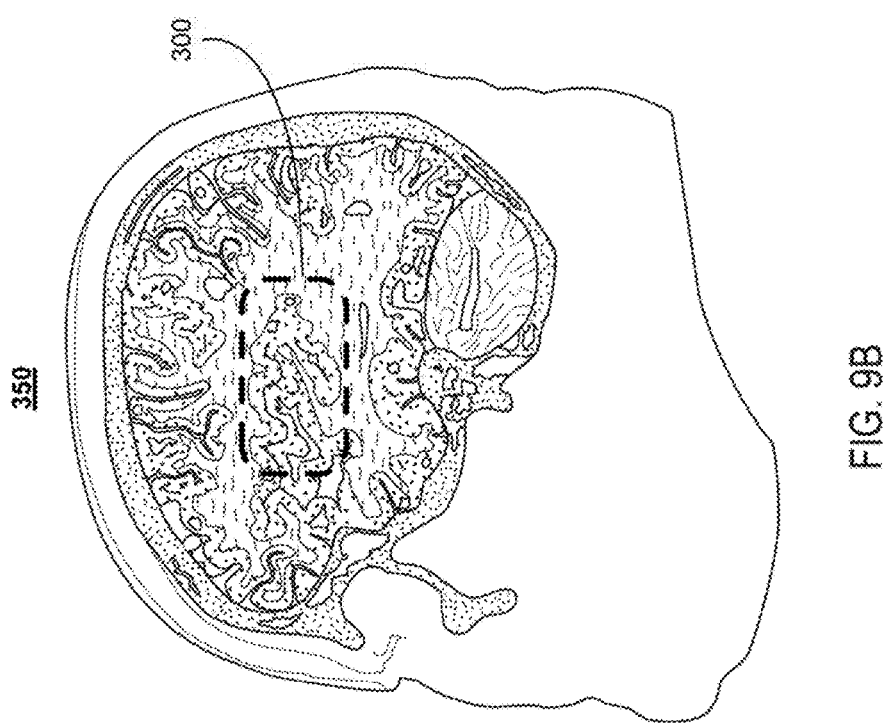

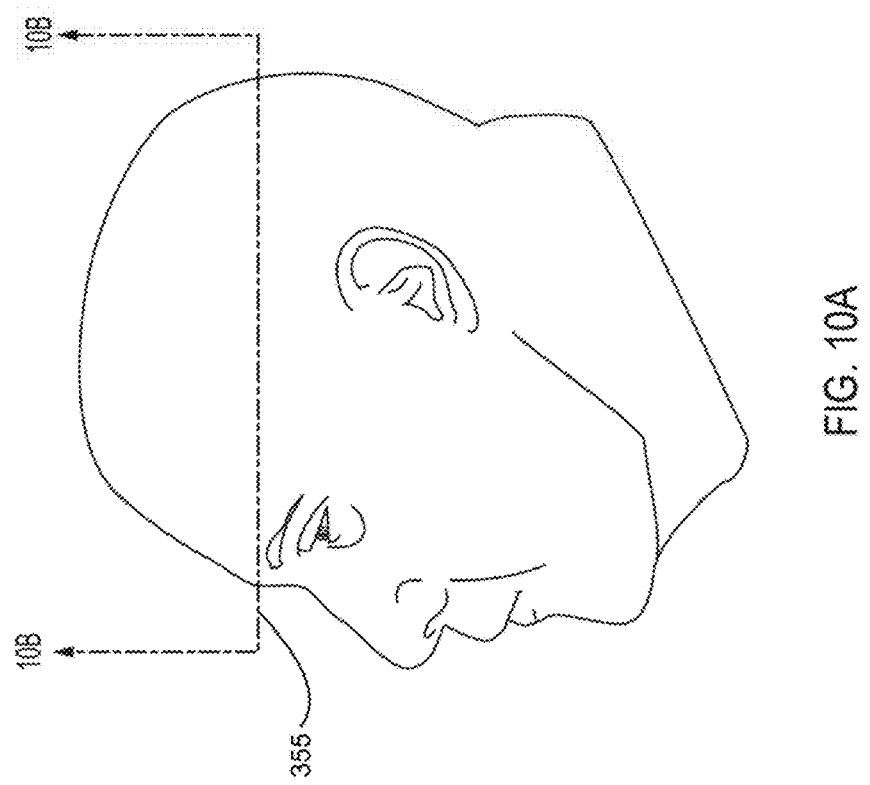

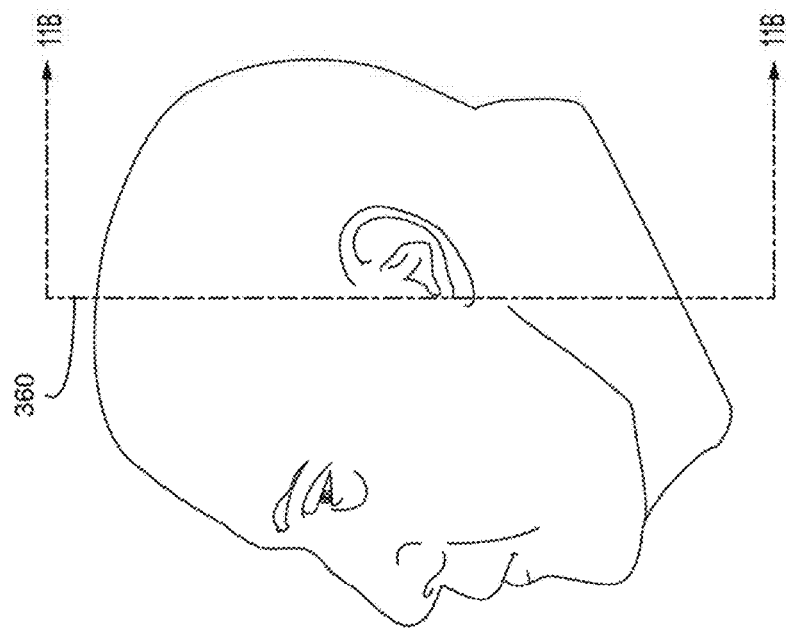

TREATMENT OF AUTOIMMUNE DISEASES WITH DEEP BRAIN STIMULATION

CROSS-REFERENCE TO RELATED APPLICATIONS

This application claims the benefit of and priority to U.S. Provisional Patent Application No. 62/290,101, filed on Feb. 2, 2016. This application is also a continuation-in-part of U.S. patent application Ser. No. 15/281,468, filed on Sep. 30, 2016, which is a continuation of U.S. patent application Ser. No. 14/470,423, filed on Aug. 27, 2014 and now issued as U.S. Pat. No. 9,474,894. The contents of the foregoing applications are herein incorporated by reference in its entirety.

BACKGROUND OF THE DISCLOSURE

With autoimmune diseases, the immune system is directed against the endogenous structures of the body. T-cells can play a role in identifying the endogenous structures as foreign to the body when not properly suppressed by regulatory T-cells. The cause of the failure of the regulatory T-cells to regulate the T-cells may be unknown. The loss of regulation can result in an inflammatory reaction on the humoral and cellular levels which, depending on the entity of the autoimmune disease, can lead to the damage of various organs.

SUMMARY OF THE DISCLOSURE

The present disclosure discusses the electrical stimulation of the brain using an electrode attached to an implantable pulse generator. In some implementations, the system described herein uses electrical stimulation to treat an autoimmune disease, such as rheumatoid arthritis and Crohn's disease. The therapy is performed by an implantable pulse generator attached to at least one electrode lead. The electrode lead is surgically implanted in or near a brain target that is related to the pathology. The neural tissue near the distal end of the electrode lead can be stimulated with electrical signals transmitted from the implantable pulse generator. The electrical stimulation may be carried out continuously or intermittently. In some implementations, the electrode lead is segmented to provide a directional electrode. The directional electrode can enable the electrical stimulation to be directed toward predetermined neurological targets. The targeting of the electrical stimulation can reduce side effects caused by the electrical stimulation. In some implementations, the electrode lead can also be used to record from the brain anatomy a signal. The recorded signal can be analyzed for indications of an autoimmune disorder, and then the brain anatomy can be stimulated to reduce the symptoms of the autoimmune disorder.

According to one aspect of the disclosure, a method for treating an autoimmune disorder includes implanting an implantable stimulator into a patient. The method can include implanting an electrode lead into the patient. The electrode lead can include a MEMS film. The MEMS film can include a plurality of electrodes, a plurality of periphery traces at least partially encircling each of the plurality of electrodes, and at least two connection points coupling each of the plurality of periphery traces with a respective one of the plurality of electrodes. The method can include driving the electrode lead toward a first target location in the brain of the patient. The first target location can include one of a first, a second, a third, or a fourth gyms of an anterior insular cortex; a superior-anterior insula; an inferior-anterior insula; an anterior-anterior insula; a posterior-anterior insula; a large insular gyms of a posterior insula; a superior-posterior insula; or an inferior-posterior insula. The method can include generating, by the implantable stimulator, an electrical signal. The method can include delivering the electrical signal to the first target location via at least one of the plurality of electrodes.

The method can include treating an autoimmune disorder with the electrical signal. The autoimmune disorder can include at least one of rheumatoid arthritis; psoriasis; psoriatic arthritis; spondyloarthritis; collagenosis; vasculitis; guillain-barré syndrome; morbus chrohn; ulcerative colitis; igg4-related disease; osteoarthritis; fibromyalgia; and Marie-Bamberger syndrome.

The method can include driving a second lead toward a second target location located on a contralateral side of the patient with respect to the first target location. The at least one of the plurality of electrodes can be a directional electrode. The method can include recording neurological activity from the target location, and selecting a portion of the plurality of electrodes to deliver the electrical signal based on the recorded neurological activity.

The method can include detecting a presence of an autoimmune disorder symptom, and increasing a characteristic of the electrical signal. The characteristic of the electrical signal can be at least one of an amplitude, a frequency, and a pulse width. The method can include detecting a presence of a side effect caused at least partially by the electrical signal and decreasing a characteristic of the electrical signal.

The method can include determining neurological activity of the target area is below a predetermined threshold and applying the electrical stimulation with a frequency between about 120 Hz and about 140 Hz. The method can include determining neurological activity of the target area is above a predetermined threshold, and applying the electrical stimulation with a frequency between about 40 Hz and about 60 Hz.

The at least one of the plurality of electrodes can be an omnidirectional electrode. The omnidirectional electrode can be a recording electrode. The MEMS film can include a ribbon cable that extends form a distal end of the MEMS film and into a lumen defined by the MEMS film. The ribbon cable can include a plurality of contact pads. Each of the plurality of periphery traces can be coupled to one of the plurality of contact pads. Each of the plurality of electrodes can include a second metal layer. The second metal layer can include at least one of platinum, iridium oxide, or titanium.

The method can include generating the electrical signal with a frequency between about 2 Hz and about 500 Hz. The method can include generating the electrical signal with a pulse width between about 10 µs and about 500 µs. The method can include generating the electrical signal with a current between about 0.1 mA and about 12 mA. The method can include selecting a different one of the at least one of the plurality of electrodes for delivering the electrical signal. The method can include delivering the electrical signal to the first target location via the different one of the at least one of the plurality of electrodes.

BRIEF DESCRIPTION OF THE DRAWINGS

The figures, described herein, are for illustration purposes. In some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings. The systems and methods may be better understood from the following illustrative description with reference to the following drawings in which:

FIG. 1 illustrates an example system for treating autoimmune diseases.

FIG. 2 illustrates the example electrode lead for use in the system illustrated in FIG. 1.

FIGS. 4C-4E illustrate a MEMS film with electrodes with redundant periphery traces for use in the system illustrated in FIG. 1.

FIG. 9B illustrates a magnetic resonance imaging (MRI) image at the sagittal section illustrated in FIG. 9A.

FIG. 10A illustrates the position of a plane of a horizontal section though a patient.

FIG. 11A illustrates the position of a plane of a coronal section though a patient.

DETAILED DESCRIPTION

Figure 3A:
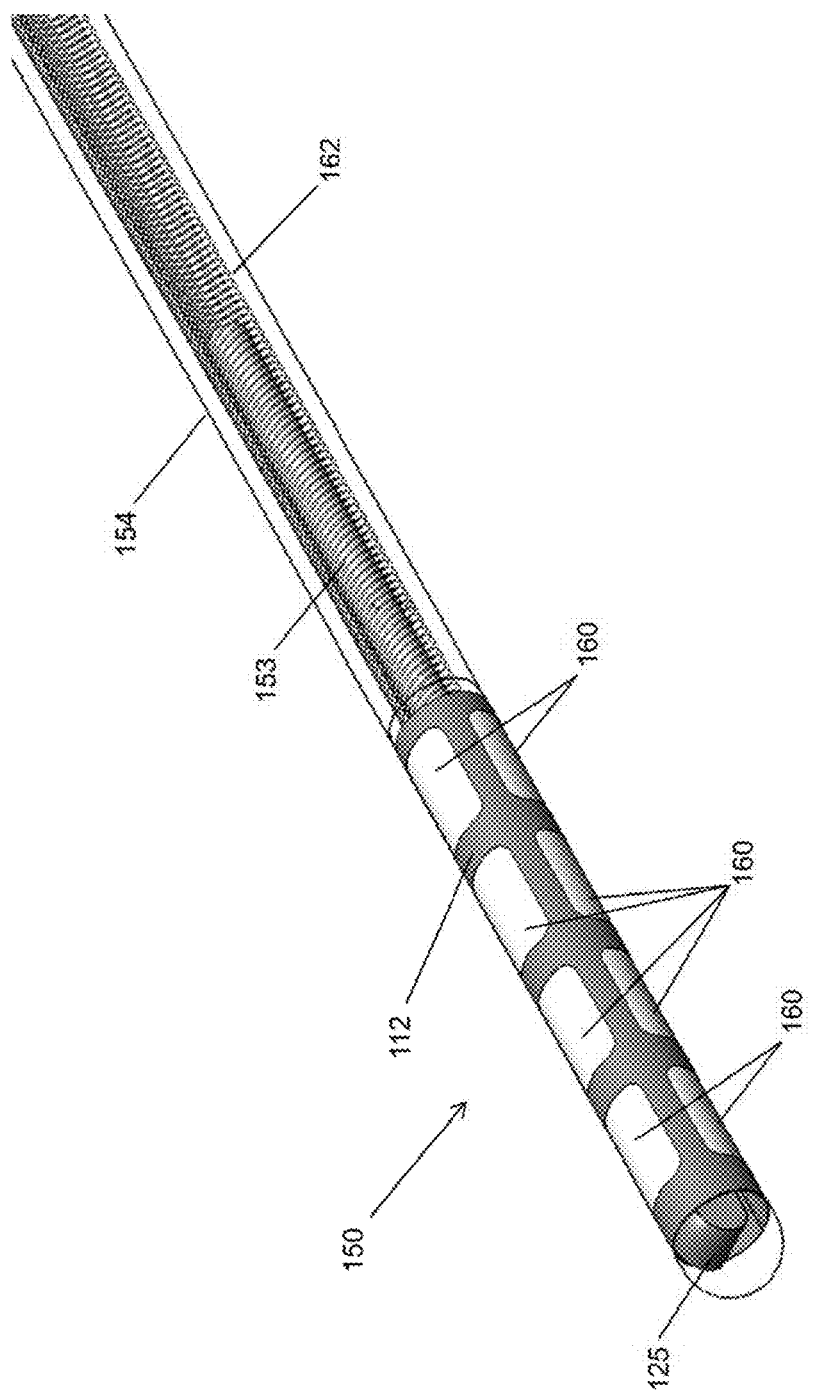
FIGS. 3A-3C illustrate example distal end of the electrode lead for use in the system illustrated in FIG. 1.

The various concepts introduced above and discussed in greater detail below may be implemented in any of numerous ways, as the described concepts are not limited to any particular manner of implementation. Examples of specific implementations and applications are provided primarily for illustrative purposes.

FIG. 1 illustrates an example system 101 for treating autoimmune and other diseases. The system 101 includes an implantable pulse generator (IPG) 110 implanted in the chest of a patient 100. The IPG 110 can be implanted below the patient's clavicle or in other areas. An extension cable 120 couples the IPG 110 to an electrode lead 130. A plurality of electrode leads 130, each coupled to the IPG 110 by an extension cable 120 can be implanted in the patient 100. As illustrated, the electrode leads 130 are implanted into the brain 140 of the patient 100.

The system 101 can include the IPG 110. The IPG 110 is configured to generate electrical signals that are transferred to the target tissue via the extension cable 120 and electrode lead 130. In some implementations, the IPG 110 is also configured to record electrical activity generated by the brain target and detected by the electrode lead 130. The IPG 110 can be configured to supply a range of electrical signals to target tissue (e.g., the brain 140) by adapting a pulse frequency, a pulse width, a pulse amplitude, or any combination thereof. The IPG 110 can generate pulse frequency ranges between about 2 Hz and about 1 kHz, between about 2 Hz and about 500 Hz, or between about 2 Hz and about 250 Hz. In some implementations, the IPG 110 is configured to excite neural activity (also referred to increasing neural activity) at a brain target or inhibit neural activity (also referred to as decreasing neural activity) at the brain target.

For example, electrical stimulations around about 50 Hz (e.g. between about 40 Hz and about 60 Hz) can induce neuro-excitation and electrical stimulations around about 130 Hz (e.g., between about 120 Hz and about 140 Hz) can induce neuro-inhibition. Pulse widths ranges can be between about 1 μs and about 1000 μs, between about 10 μs and about 500 μs, or between about 80 μs and about 120 μs. The pulse amplitudes may range from about 50 μA to about 15 mA, between about 100 μA and about 12 mA, or between about 1 mA and about 3 mA. In some implementations, the IPG 110 is voltage driven, and the pulse amplitude is between about 0.1 V and about 10 V or between about 2 V and about 4 V. These ranges are examples and other ranges are possible. The stimulation parameters can be patient or disease specific and can vary over the course of the patient's treatment. For example, the stimulation parameters can be increased over time if the patient's body begins to encapsulate the electrodes of the electrode lead 130. Different stimulation parameters may induce different neurological responses in the patient, including improved or decreased beneficial effects and decreased side effects. In some embodiments, the stimulation is continuous, for example lasting days, weeks, months, or years. Over the course of the continuous stimulation, the stimulation may be delivered intermittently. For example, the stimulation may be provided for 10 minutes every hour over the course of 1 month.

In some embodiments, the IPG 110 is configured to capture and record signals from the brain or other target tissue. The captured signals can be analyzed to determine if the signals are indicative of a disease state. For example, in some neurological disease states, it is possible to determine a brain volume directly affected by the disease state by its lack of neurophysiological activity, or inversely by its overactive neurophysiological activity. By performing recordings from the distal end 150 of the electrode lead 130, neurophysiological marker signals can be recorded and analyzed by a machine learning algorithm to determine if the disease state is present. Thresholds can be set to indicate whether the neurophysiological activity is in an "inactive" state or an "active" state. The recorded signals also can be presented to the physician via a telemetric connection with the IPG 110. The physician can make a decision as to which electrodes of the electrode lead 130 is best placed to use for therapeutic stimulation. In some implementations, the IPG 110 includes a signal processing algorithm that independently determines which electrodes of the electrode lead 130 to use to deliver the electrical stimulation to without physician intervention. This can be referred to herein as a closed-loop stimulation.

FIG. 2 illustrates an example stimulation lead 130. The stimulation lead 130 includes a body. The body may also be referred to as a tube body, tube, or catheter. The body includes several orientation markers 156. At a distal end 150, the stimulation lead 130 includes a MEMS film with a plurality of electrodes 160. At a proximal end 142, the stimulation lead 130 includes a plurality of contacts 145.

At the proximal end 142 of the stimulation lead 130, the stimulation lead 130 includes one or more contacts 145. The contacts 145 can be used to establish an electrical connection between the electrodes 160 of the MEMS film and the IPG 110. For example, each of the contacts 145 can be coupled with one or more electrodes 160 of the MEMS film via lead wires that run the length of the stimulation lead 130. The stimulator 122 may be coupled with the contacts 145 through a plurality of cables 120 to stimulate tissue or record physiological signals.

The distal end 150 of the stimulation lead 130 can include a MEMS film that includes a plurality of electrodes 160. FIGS. 3A-4B illustrate example distal ends 150 and example MEMS films in greater detail.

The distal end 150 of the electrode lead 130 can have a diameter between about 1 mm and about 1.5 mm (e.g., +/−10%). In some implementations, the electrode lead 130 can have the same diameter along its length. A substantial portion (e.g., between about 60% and about 95%) of the electrode lead 130 can be hollow, enabling a rigid stylet to provide support to the electrode lead 130 during the implantation procedures. The stylet can be removed during the surgery once the electrode lead 130 is positioned at its final target. The electrode lead 130 can be implanted in its target position through a surgically prepared hole in the skull. Each hemisphere of the brain can receive at least one electrode lead 130. Each of the electrode leads 130 is coupled to the IPG 110 via an extension cable 120.

FIG. 3A illustrates an example of the distal end 150 and example MEMS film 112 in greater detail. The MEMS film 112 can be wrapped or assembled around the distal end 150 of the body 154 of the electrode lead 130 or formed into a semi-rigid cylinder that is coupled to the end of the body 154. The MEMS film 112 can be formed into a semi-rigid cylinder by heat rolling the MEMS film 112 and back filling the lumen formed by the rolled MEMS film with an epoxy. The MEMS film 112 includes a plurality of electrodes 160. The MEMS film 112 can also include a ribbon cable 125 that wraps over the most distal end of the MEMS film 112 and extends into a lumen defined by the MEMS film 112. The ribbon cable 125 can be coupled with one or more lead wires 162, which can in turn be coupled with the contacts 145. A portion of the length of the lead wires 162 are wrapped around a stylet 153.

The MEMS film 112 can include one or more electrodes 160. As illustrated, the MEMS film 112 includes 12 electrodes—three electrodes placed around the circumference of the MEMS film 112 at four different longitudinal locations along the length of the electrode lead. In some implementations, the MEMS film 112 can include between about 6 and about 64 electrodes, between about 8 and about 32, between about 8 and about 24, or between about 8 and about 12 electrodes. The electrodes 160 can be configured as directional electrodes or omnidirectional electrodes. Omnidirectional electrodes may wrap substantially around (e.g., at least 80%, or at least 90%) the circumference MEMS film 112 when the MEMS film 112 is formed into a cylinder, and the directional electrodes may wrap only around a portion of the circumference (e.g., less than 80%) the planar formed, cylindrical MEMS film 112. One or more directional electrodes can electrically couple to form an omnidirectional electrode. For example, the three distal most electrodes 160 may be electrically coupled together to form an omnidirectional electrode at the tip of the stimulation lead 130. In some implementations, the MEMS film 112 can include a plurality of omnidirectional electrodes and a plurality of directional electrodes. For example, the electrodes 160 may be configured as two omnidirectional electrodes and six directional electrodes. The omnidirectional electrodes can be configured as recording electrodes. The omnidirectional electrodes can be configured as stimulating electrodes. The directional electrodes can be configured as recording electrodes. The directional electrodes can be configured as stimulating electrodes.

Electrical traces running through the MEMS film 112 can couple each of the electrodes 160 with one or more of the lead wires 162. The traces may run under an insulative layer of the MEMS film 112 to the ribbon cable 125, where the traces terminate and are coupled with the one or more lead wires 162. In some implementations, the stimulation lead 130 includes one lead wire 162 for each of the electrodes 160. In other implementations, the stimulation lead 130 includes fewer lead wires 162 than electrodes 160 because one or more of the lead wires 162 are electrically coupled with more than one of the electrodes 160. For example, when the MEMS film 112 includes two omnidirectional electrodes and six directional electrodes, the stimulation lead 130 may include eight lead wires 162. The lead wires 162 can run along the length of the body toward the proximal end 142 of the body. The lead wires 162 may traverse the length of the body within the lumen of the body. At the proximal end 142 of the MEMS film 112, the lead wires 162 may be electrically coupled with the contacts 145.

Figure 3B:
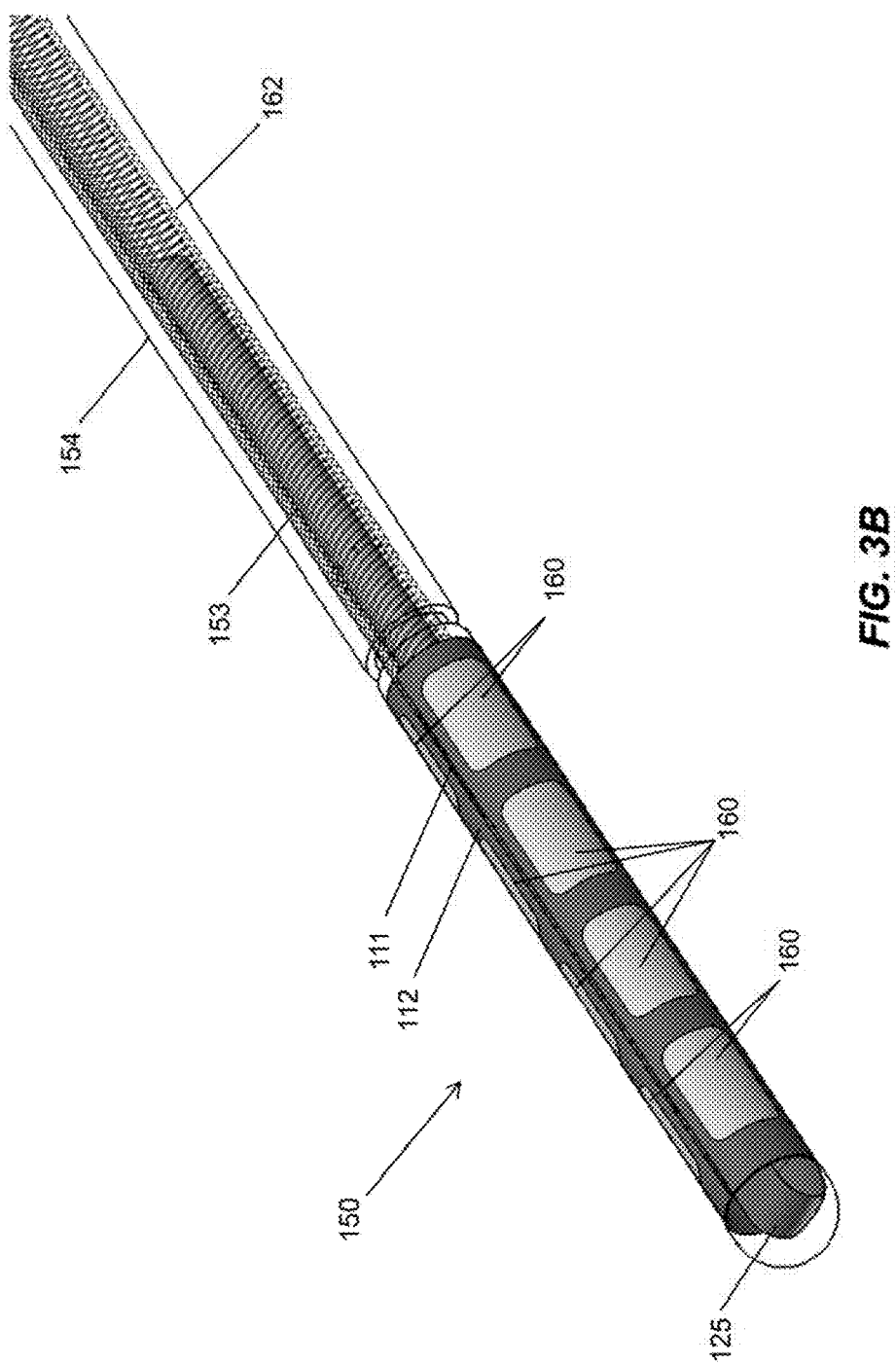

FIG. 3B illustrates the underside of the distal end 150 of the stimulation lead 130 illustrated in FIG. 3A. The MEMS film 112 can be initially formed as a planar film that is formed into a cylinder. This method of forming the MEMS film 112 can create a connecting seam 111.

The MEMS film 112 can include a plurality of layers. In some implementations, the MEMS film 112 includes five layers. The five layers can include a first polymeric layer and a first silicon based barrier layer that is at least partially deposited (or otherwise disposed) over the first polymeric layer. The MEMS film 112 can also include a first metal layer that is at least partially deposited (or otherwise disposed) over the first silicon based barrier layer. Other layers can include a second silicon based barrier layer at least partially deposited (or otherwise disposed) over the first metal layer and the first silicon based barrier layer. The second silicon based barrier layer can define a first plurality of through-holes over portions of the first metal layer. Another layer of the MEMS film 112 can be a second polymeric layer that is at least partially deposited (or otherwise disposed) over the second silicon based barrier layer. The second polymeric layer can also define a plurality of through holes. The plurality of through-holes of the second silicon based barrier layer and the second polymeric layer are substantially aligned to define each of the plurality of electrodes 160 and contact pads 145 of the MEMS film 112.

Figure 3C:
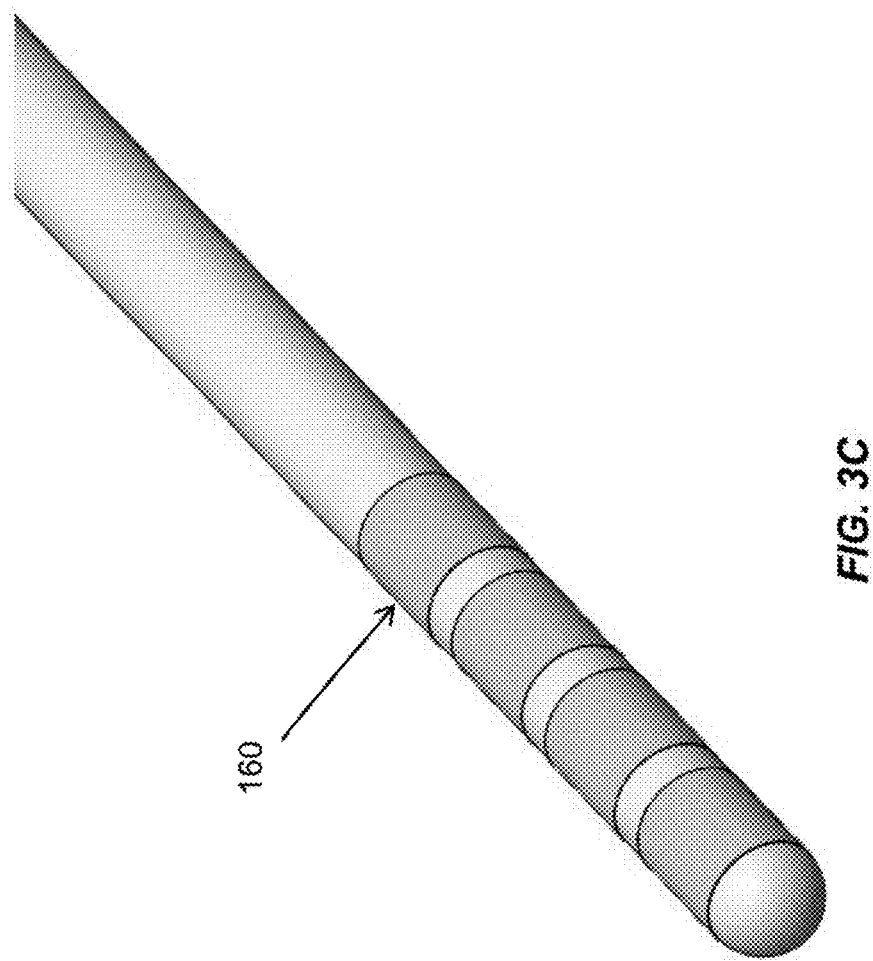

FIG. 3C illustrates another example of the distal end 150 of the electrode lead 130, in greater detail. The distal end 150 of the electrode lead 130 includes a plurality of electrodes 160. As illustrated, the distal end 150 includes four electrodes 160. The electrodes 160 are configured as cylindrical electrodes (also referred to as ring electrodes). In some implementations, electrodes 160 configured as cylindrical electrodes can emit an electrical stimulation that radiates out from the electrodes 160 in a substantially uniformly pattern around the circumference of the electrodes 160. Each of the electrodes 160 is individually addressed by the IPG 110 via the proximal electrical contacts 145. The distal end 150 is positioned near the brain target using stereotactic techniques. The one or more of the electrodes 160 can be used as both a stimulating and a recording electrode, or the one or more of the electrodes 160 can be used as only a stimulating electrode or only a recording electrode. In some implementations, the distal end 150 can include a combination of omnidirectional electrodes and directional electrodes.

Figure 4B:
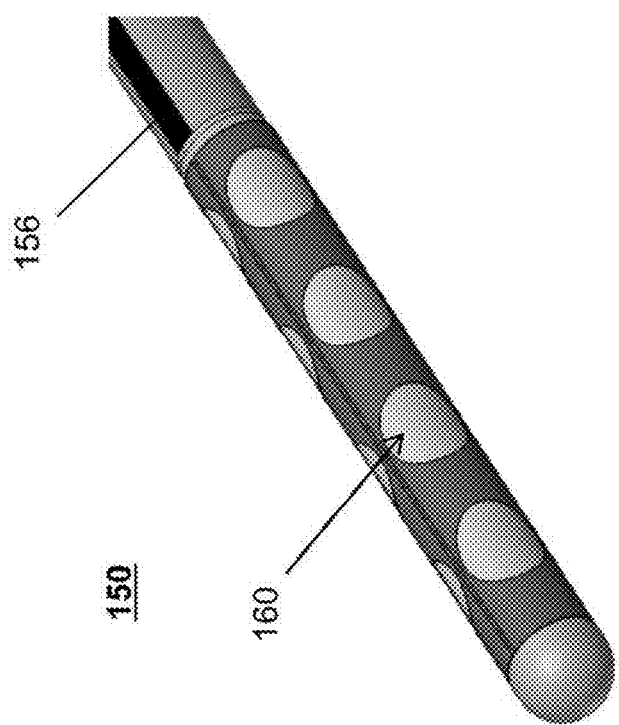
FIGS. 4A and 4B illustrate the distal end of the electrode lead for use in the system illustrated in FIG. 1.
Figure 4A:
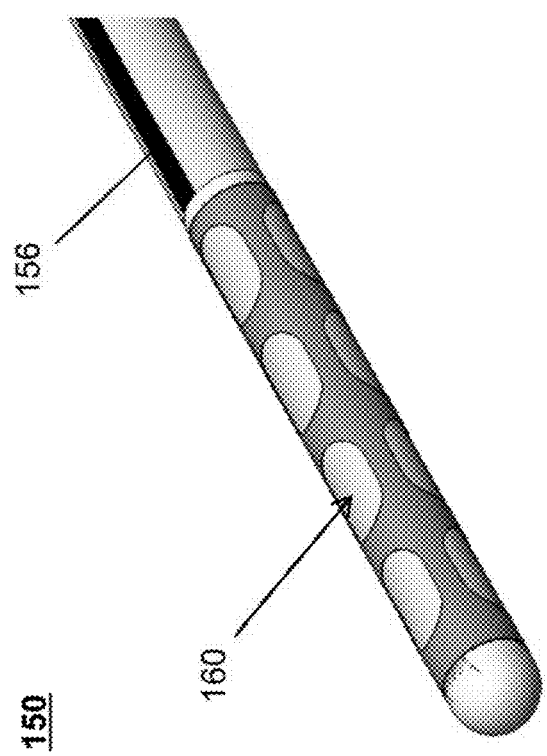

FIGS. 4A and 4B illustrate the distal end 150 of the electrode lead 130 where the electrodes 160 are configured as directional electrodes. As illustrated in FIG. 4A, the distal end 150 includes oval shaped electrodes 160. The distal end 150 of the electrode lead 130 includes twelve electrodes 160. The electrodes 160 are configured in three columns around the circumference of the distal end 150. Each column of electrodes 160 includes four electrodes 160. Each of the electrodes 160 can roughly cover an arc angle around the circumference of the distal end 150 of about 90 degrees (e.g., +/−10 degrees). In other implementations, the distal end 150 may include between 1 and 8 columns of electrodes, with each column including between 1 and 10 electrodes 160. In some implementations, each of the electrodes 160 have a length along the distal end 150 of between about 0.25 mm and about 2 mm. Each of the electrodes 160 can be individually addressed by the IPG 110 to enable directional stimulation and recording. In some implementations, the electrodes 160 configured as directional electrodes are used in areas of the brain where a dense quantity of neurological functions exist, such as the insular cortex. Directional electrodes can enable the targeted electrical stimulation to a predetermined volume Avoiding other volumes of the brain can reduce the side effects.

In some implementations, the stimulation (both the characteristics of the stimulation signal and the election of which electrodes 160 to use in the stimulation processed) are tuned based on bio-feedback. For example, a patient may experience relief from their disease symptoms, but experience a side effect. Therefore, the physician can choose to decrease the pulse amplitude on an active electrode until the side effects diminish, but the beneficial effect remains. This trial-and-error procedure can provide better electrode selection, pulse frequencies, pulse widths, and pulse amplitudes. Moreover, as the disease state progresses, the trial-and-error procedure enables updating of the stimulation parameters.

Each of the electrodes 160 in a given row of the distal end 150 can be electrically coupled together to create an omnidirectional electrode. The distal end 150 also includes orientation markers 156. A surgeon may orient the orientation marker 156 normal to a known plane, such as the sagittal plane, or along a known plane to enable the surgeon to know in which direction each of the electrodes 160 is facing.

FIG. 4B illustrated another example distal end 150 of the electrode lead 130. The electrodes 160 of the distal end 150 are configured as directional electrodes, as described above in relation to FIG. 4A. Each of the electrodes 160 is configured in a circular shape. In other implementations, the electrodes 160 can be square in shape or have any other polygonal shape.

Figure 4C:
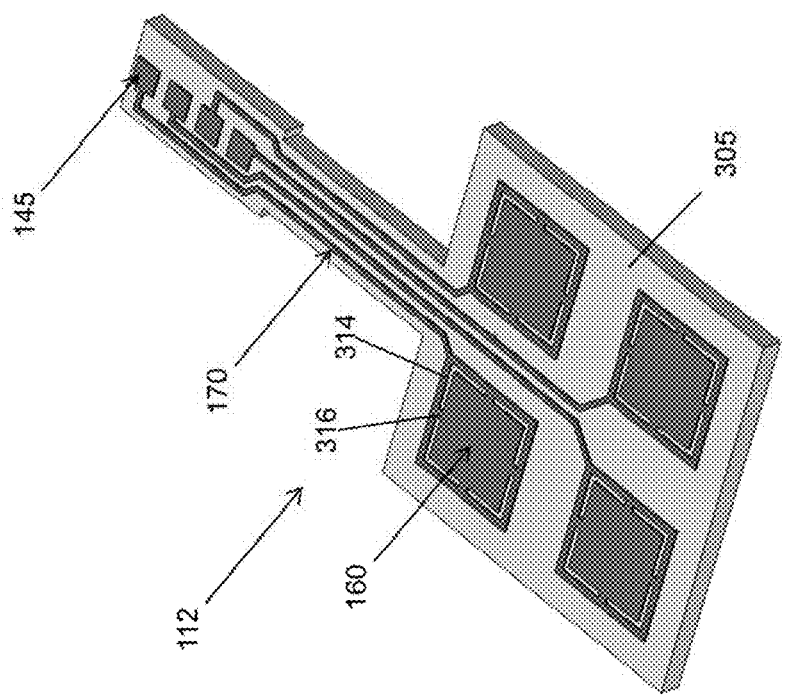

FIG. 4C illustrates a MEMS film in a planar configuration (prior to being formed into a cylinder) with electrodes 160 that include redundant periphery traces. As illustrated a metal layer is deposited onto a polymeric layer 305. The metal layer can include the contact pads 145, the traces 170, the periphery traces 314, and the electrodes 160. Each periphery trace 314 can extend around the perimeter of an associated electrode 160. The periphery traces 314 can fully or partially encircle each of the plurality of electrodes 160. As illustrated in FIG. 4C, the periphery traces 314 fully encircle each of the plurality of electrodes 160 by extending around the perimeter of the electrodes 160. The periphery trace 314 can be coupled with an electrode 160 at a plurality of connection points 316. Each electrode 160 can include four connection points 316. In some implementations, each electrode 160 includes one or more connection points 316 per edge of the electrode 160. For example, the electrodes 160 can be squares with four edges and one connection point 316 per edge. The connection points 316 can be placed on opposite sides of the electrodes 160. In some implementations, the contact pads 145 can also be surrounded by a periphery trace 314.

A second metal layer can be deposited onto at least a portion of the electrodes 160. The second metal layer can include at least one of platinum, iridium oxide, or titanium.

FIGS. 4D and 4E illustrate the application of a second polymeric 325 (or isolating layer) to the first isolating layer 305 illustrated in FIG. 4C. The second polymeric layer 325 can include a plurality of through holes 171 that align with the electrodes 160 and the contact pads 145. The silicon based barrier layer that can be deposited over the metal layer can also include a plurality of through holes that align with the through holes 171 of the second polymeric layer. The second polymeric 325 can be bonded to the surface of the first polymeric layer 305 and the metal conductive layer. The second polymeric 325 can be photolithographically defined. The resulting stack of layers is demonstrated in FIG. 4E, where the electrodes 160 and corresponding contact pads 145 are apparent through the through holes 171, but the traces 170 and periphery traces 314 are hidden from view and electrically isolated from the outside environment.

Figure 5:
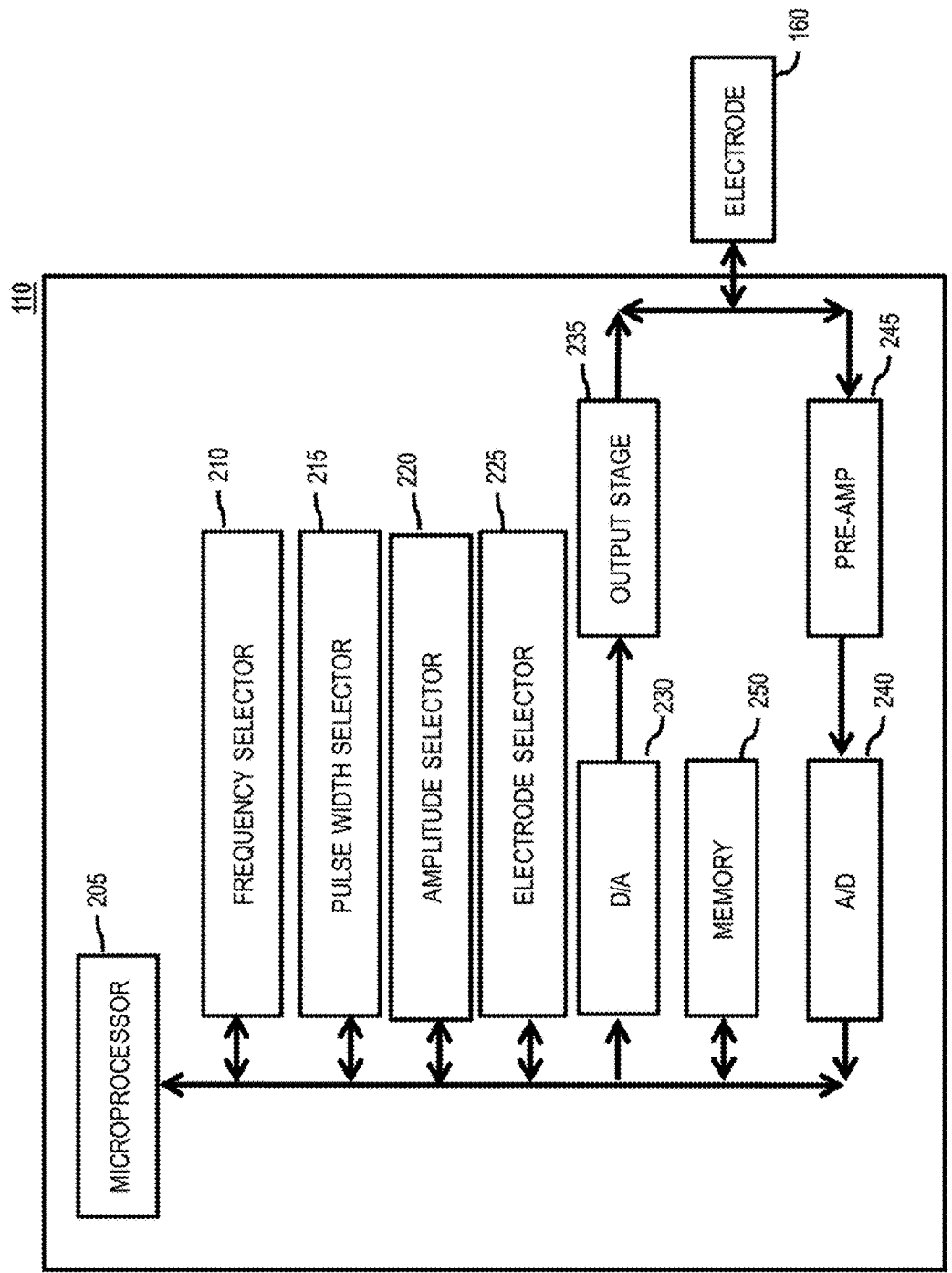
FIG. 5 illustrates a block diagram of the components of an implantable pulse generator for use in the system illustrated in FIG. 1.

FIG. 5 illustrates a block diagram of the components of the IPG 110. The IPG 110 can include a microprocessor 205 that can coordinate and control the function of the IPG 110. The microprocessor 205 can execute any script, file, program, application, set of instructions, or computer-executable code that is stored in the memory 250, which can cause the microprocessor 205 to perform the functions of the components of the IPG 110. The IPG 110 can include a frequency selector 210. The frequency selector 210 can select and adjust the frequency of the electrical stimulation used to stimulate the target tissue. The IPG 110 also includes a pulse width selector 215 that can select and adjust the pulse width of the electrical stimulation. For example, the pulse width selector 215 can select a pulse width of the electrical stimulation between about 10 µS and about 500 µS. The IPG 110 can also include an amplitude selector 220 that can be configured to select the amplitude of the electrical stimulation between about 10 µA and about 15 mA. The amplitude selector 220 can also select whether the amplitude of the electrical stimulation is current driven or voltage driven. The electrode selector 225 can select to which of the electrodes 160 the electrical stimulation is delivered. The electrode selector 225 can also select which of the electrodes 160 are used as stimulating electrodes and which of the electrodes 160 are used as recording electrodes. Any of the above described selectors can be configured as software, scripts, or applications executed by the microprocessor 205.

The IPG 110 also includes a digital to analog (D/A) convertor 230. The D/A converter 230 is configured to output the electrical stimulation signals to an output stage 235. The output stage 235 can amplify the analog signal, change the impedance of the signal, filter, or otherwise change the characteristics of the signal. The output stage 235 can then direct the analog signal to the electrodes 160 as a stimulation signal. The IPG 110 can be configured to capture and record electrical signals from the target tissue. The IPG 110 includes a pre-amplifier 245. The pre-amplifier 245 amplifies the signals captured by the electrodes 160 and provided to the IPG 110. The signals are captured as analog signals that are converted to a digital signal by an analog to digital (A/D) convertor 240. The digitized signal can then be stored in the memory 250. The microprocessor 205 can retrieve signals stored in the memory 250 and transmit the signals to an external computer or display for viewing by a physician or healthcare professional. The memory 250 can also store programs, scripts, applications, and procedures, executed by the microprocessor 205.

Figure 6:
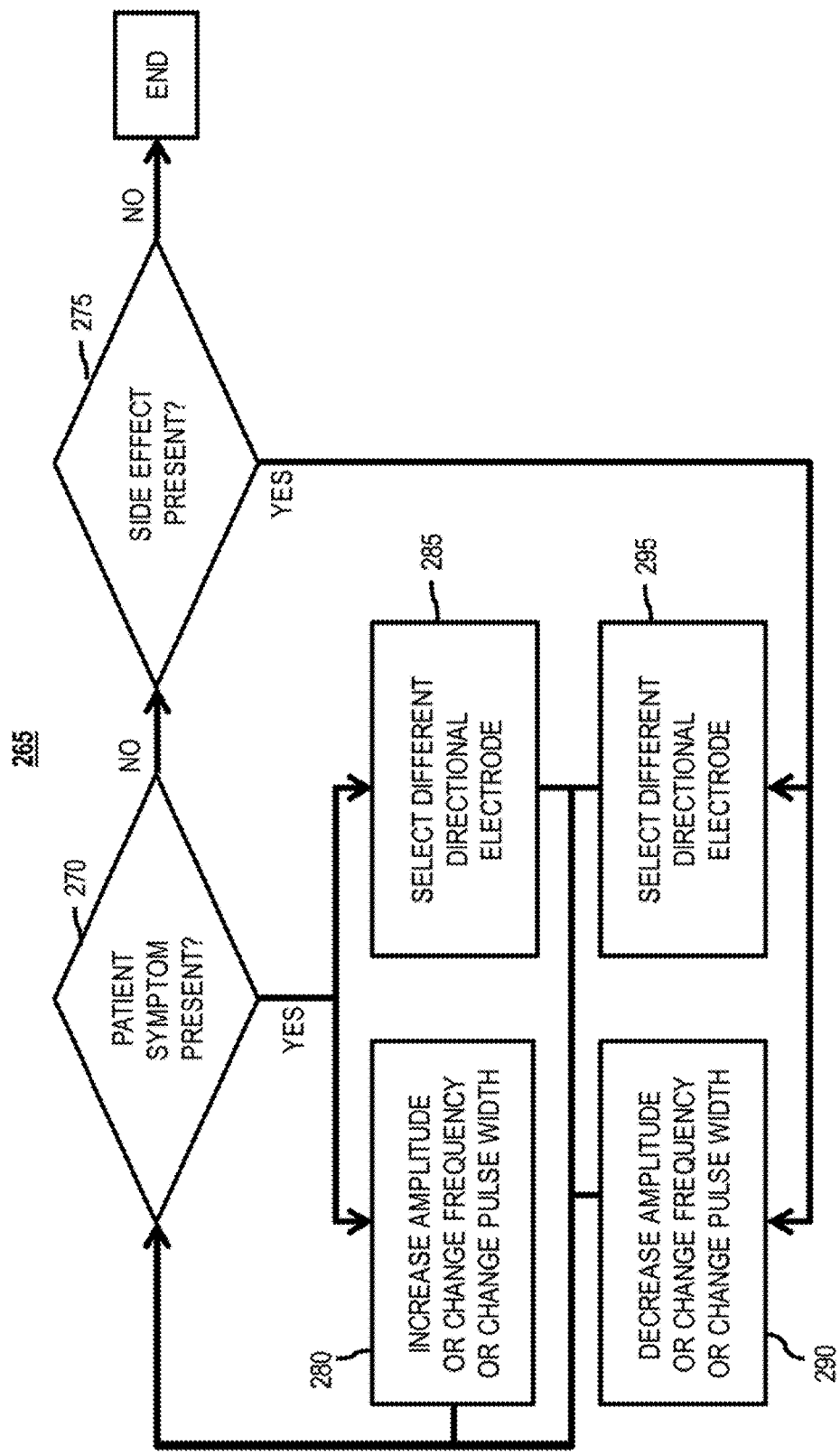
FIG. 6 illustrates a flow chart of a method for tuning the electrical stimulation delivered to a patient using the system illustrated in FIG. 1.

FIG. 6 illustrates a flow chart of a method 265 for tuning the electrical stimulation delivered to a patient. The method 265 includes determining if symptoms are present (step 270). If symptoms are present, the method 265 can include selecting a different one of the electrodes used to stimulate the patient (step 285). The method 265 can also include increasing one or more of the characteristics of the electrical stimulation (step 280). After a predetermined amount of time, it could be re-determined whether the patient is experiencing symptoms (step 270).

As set forth above, the method 265 begins with the determination of whether a patient is experiencing symptoms (step 270). Either prior to performing step 270 or after performing step 270, one or more electrode leads described herein can be implanted into or near a target location. The electrode leads can be implanted by driving the electrode leads towards the target location. The location of the electrode lead can be confirmed using stereotaxic procedures, imaging procedures, or by making recordings with the electrode lead to determine if characteristic signals from the target location are recorded. The target location can include a first, a second, a third, or a fourth gyms of an anterior insular cortex; a superior-anterior insula; an inferior-anterior insula; an anterior-anterior insula; a posterior-anterior insula; a large insular gyms of the posterior insula; a superior-posterior insula, an inferior-posterior insula; a volume within several centimeters of the insula that project to or from the insula. In some implementations, second electrode lead can be implanted at a second target location that can be on the contralateral side of the brain from the first target location.

The symptoms detected in step 270 can be those related to rheumatoid arthritis, Crohn's disease, or any of the other diseases described herein. At step 280, the characteristics of the electrical signal generated by the IPG, and delivered to the target location, can be increased. In some implementations, the characteristic is the amplitude of the electrical stimulation signal. For example, the amplitude can be increased over a period of time as the medical professional monitors the patient for side effects from the increased stimulation. Other characteristics can include the frequency or the pulse width of the stimulation signal. If the symptom is due to an over excitation of the target location, the frequency of the electrical stimulation signal can be set to be between about 40 Hz and about 60 Hz. If the symptom is due to an under excitation of the target location, the frequency of the electrical stimulation signal can be set to be between about 120 Hz and about 140 Hz.

At step 285, the method 265 can also include selecting a different directional electrode through which to deliver the electrical stimulation signal. The characteristics of the electrical stimulation signal delivered to the newly selected directional electrode can be the same as previously delivered electrical stimulation signals, or step 280 can also be performed and new characteristics can be selected that can be delivered through the newly selected directional electrode. As illustrated below in reference to FIGS. 24 and 25, the selection of a new direction electrode can be made to direct the electrical stimulation signal toward the target location and away from regions of the brain that might cause side effects.

If at step 270, it is determined the patient is not experiencing symptoms, it is determined whether side effects are present (step 275). If side effects are present, the method 265 can include selecting a different electrode (step 295) or decreasing one or more of the characteristics of the electrical stimulation (step 290). Decreasing the characteristics of the electrical stimulation can reduce the effect of the stimulation and side effects because the electrical stimulation may not effect as large of a volume of the target tissue. Selecting a different electrode can reduce the side effects because the new electrode may stimulate another portion of the target volume, which may control different or fewer functions. Once the one or both of the steps 290 and 295 are completed, after a predetermined amount of time the method 265 can begin. In some implementations, the method 265 may be repeated within minutes, hours, days, weeks, or months. The time between repeating the method 265 may be dependent on the amount of time it takes for physiological manifestations to appear. For example, is the physiological manifestation to be measured is a change in heart rate, the change in heart rate may occur almost immediately upon completion of the method 265. Other physiological manifestations, such as the decrease of tnf-a or il-6 may take hours to days to appear. If the patient is not experiencing a symptom at step 270 or a side effect at step 275, the method 265 ends. If the patient is not experiencing a symptom at step 270 or a side effect at step 275 the method can continue until the best electrode and stimulation characteristics are selected for the patient. In some implementations, the method 265 may be continued until the patient symptoms are reduced at step 270 and the side effects are reduced at step 275 rather than eliminated.

In some examples, after placement of the electrode 160, the electrode 160 can initially be driven at frequencies between about 2 Hz and about 500 Hz, between about 50 Hz and about 400 Hz, or between about 100 Hz and about 250 Hz to reduce neural activity in the target tissue. The stimulation signal applied to the electrode 160 can have a pulse width between about 10 µs and about 500 µs, between about 10 µs and about 400 µs, between about 10 µs and about 300 µs, between about 10 µs and about 200 µs, or between about 10 µs and about 100 µs. The current of the stimulation signal may be between about 0.1 mA and about 12 mA, between about 0.1 mA and about 10 mA, between about 1 mA and about 8 mA, between about 1 mA and about 6 mA, or between about 1 mA and about 3 mA.

Additional embodiments exist where the frequency is significantly lower, such as 50 Hz to drive and excite neural activity as opposed to inhibiting said activity.

Disease States of Autoimmune Disorders

The system and methods described in relation to FIGS. 1-6 may be used to treat any of the autoimmune diseases described herein, such as, but not limited to those discussed below.

HLA (human leukocyte antigens) can serve for the identification of endogenous structures. HLA class I antigens are present on all nucleated cells of the body. HLA class II antigens are present on the surface of antigen-presenting cells, such as B-lymphocytes or macrophages. The genetic information for the synthesis of the HLR is located on chromosome 6, in the area of the major histocompatibility complex (MHC). T-cells can play a role in autoimmune diseases. T-cells are deactivated in the process of clonal deletion in the thymus. The thymus is a double-lobed organ in the upper mediastinum and located behind the sternum. Lymphocytes, which can identify endogenous HLA, are multiplied in a first step of clonal deletion. In a second step of clonal deletion, T-lymphocytes, which are directed against endogenous antigens, are destroyed (negative selection). The control through the nervous system (innervations) of the thymus occurs mainly sympathetically. The cell bodies of the efferent nervous cells are located in the cervical ganglion of the sympathetic trunk.

With autoimmune diseases, the immune system is directed against the endogenous structures. For example, the T-cells can play a role in identifying endogenous structures as foreign objects are not sufficiently inhibited by regulatory T-cells. In some cases, an immunological cross-reaction after exposition to a foreign antigen, such as, viruses or bacteria, is suspected as the cause of the autoimmune disease.

The triggering of aetiological factors for the formation of chronic inflammatory system disorders are largely unclear. Inflammatory mediators that closely influence each other seem to play a role in both the triggering of the acute episodes and the maintenance of autoimmune diseases. Monozyte and macrophage produced pro-inflammatory cytokines interleukin 1 (IL-1), interleukin 6 (IL-6), and tumor necrosis factor α (TNF-α) that can help control the inflammatory process. Opposite to the influence of the pro-inflammatory zytokines are the anti-inflammatory mediators, such as interleukin-1 receptor antagonist (IL-1ra), interleukin 10 (IL-10), and interleukin 4 (IL-4). The initiation and maintenance of the inflammation is largely explained by the imbalance between pro- and anti-inflammatory mediators. Some of medications used in an immunotherapy aim at improving immune-modulation (e.g., manipulating the balance between inflammation promoting and inhibiting zytokinens). This can be achieved, for example, by suppressing the secretion of pro-inflammatory zytokine. Although such inflammatory processes may possess many secondary elements, they are the main point of application in current anti-inflammatory therapy strategies.

Overview of Rheumatoid Arthritis

Rheumatoid arthritis is a chronically inflammatory system disorder, which attacks the synovial of the joints and causes the clinical picture of polyarthritis. Other organs can also be affected. The disease shows a relapsing, progressive course that leads to the destruction of the joints and can cause severe disability. The precise causes of rheumatoid arthritis are unexplained. It is an autoimmune disease where certain endogenous tissues (e.g. joint cartilage) and connective tissue are attacked by the immune system, such as antibodies and phagocytes. The disease has a genetic disposition. Rheumatoid arthritis is the most common inflammatory joint disease. Globally around 0.5-1 percent of the population is affected by rheumatoid arthritis. In Germany, the number is estimated at 800,000. Women are three times more likely to be affected than men. All age-groups can contract rheumatoid arthritis. The most commonly affected age group is between 35 and 45 years of age. According to one scientific hypothesis, the disease can be triggered by viruses or bacteria, similar to the description of the pathogenesis of the rheumatoid fever. There may be a connection between periodontitis disease and the development of rheumatoid arthritis. The current knowledge understands the pathogenetic processes as misdirected immune cells, which enter the affected joint and produce inflammation-promoting messenger substances—so-called zytokines. Promotion of the zytokines creates an inbalance. For example, interleukin 1 (IL-1), IL-6 and the tumor necrosis factor (TNF-□) are overly abundant. They are responsible for the destructive inflammatory processes in the joint tissue and the activation of bone resorption cells (e.g. osteoclasts). Through the effects of the zytokines, a tumorous tissue, the pannus, develops on the inner lining membrane of joints (synovialis), which, after a certain time, destroys cartilage, bone and other tissue of the affected joint.

The diagnosis is made clinically by counting and localization of painful, swollen, and overheated joints; patients' self-assessment; and by chemical tests. The diagnosis may be made chemically in a lab based on rheumatoid factors, such as the ACPA status (antibodies against citrullinated protein-/peptide-antigens), the blood sedimentation rate (ESR), and the c-reactive protein (CRP). Cases of seronegative arthritis are also known, as well as cases in which the person affected presents a low rheumatoid factor (RF), which it is not sufficient for a diagnosis. However, studies have shown that a seropositive RF or ACPA status points to a serious erosive course of the disease with a rapidly progressive joint destruction. Image generating procedures such as x-ray and Magnetic Resonance Tomography Imaging (MRT) examinations, can be used to assess the bone damage (erosions). Typical radiological results are subchondral osteoporosis, destruction of the surrounding bone, ankylosis, and joint malformation (button-hole deformity, swan-neck deformity, ulnar deviation). With the scintigraphy of the soft tissue and the bones, the distribution patterns of the inflammation activities of the various joints can be depicted.

During treatment, the base therapeutic methotrexate (MTX) is often administered. Due to its effectiveness and its high tolerance MTX is the "gold standard" of base therapy. Additional so-called conventional base therapeutics can include leflunomide, sulfasalazine, chloroquine and hydroxychloroquine, cyclosporine A, azathioprine, cortisone or cortisone-fee anti-inflammatories, or a combination thereof.

New therapeutics can include antibodies, soluble receptors, and antagonists, which are directed against pro-inflammatory cytokines such as IL-1, IL-6 of TNT-alpha. They are also called "biologicals." Directed against TNT-alpha are the TNF-alpha inhibitors adalimumab, certolizumab, etanercept, golimumab, and infliximab. The IL-1 receptor-antagonist is called anakinra, the IL-6 receptor-antagonist tocilizumab. The B-cell therapy with rituximab (monoclonal CD20 antibody) can be applied after the failure of the initial TNF-alpha inhibitors. With insufficient response to therapy and/or intolerance of TNF-alpha inhibitors, the treatment can be adjusted to another TNF-alpha inhibitor or biologicals with different effect mechanism such as, for example, rituximab. Upon severe joint changes that can develop in the course of the rheumatoid disease, there are also surgical treatments, such as the synovektomy, the joint resection, the arthrodesis, the arthroplasty, and the endoprosthesis, as an option.

The Insular Cortex

Figure 7:
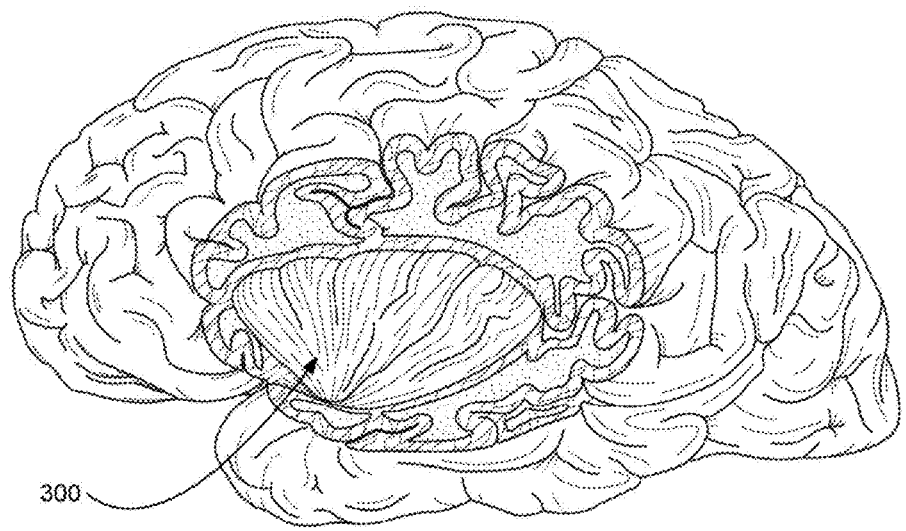
FIG. 7 illustrates a partial cross-sectional view of a human brain.

FIG. 7 illustrates a partial cross-sectional view of a human brain. The insular cortex 300 (also referred to as the insula 300) is a distinct cerebral lobe that is situated deep to the parietal lobe. Although it represents less than 2% of the total cortical area, it is connected with various regions of the central nervous system (CNS) and has been implicated in a wide range of functions. Based on the cytoarchitecture of the layers in the ventro-dorsal plane, the insular cortex 300 is sub-divided into three zones that form concentric layers, namely the rostroventral agranular zone, the caudodorsal granular zone, and the intermediate dysgranular zone. Anatomically, the insular cortex 300 is divided by the sulcus centralis insulae into the larger anterior and the smaller posterior regions. The anterior region is sometimes further subdivided into the anterior and posterior rostral divisions.

Figure 8:
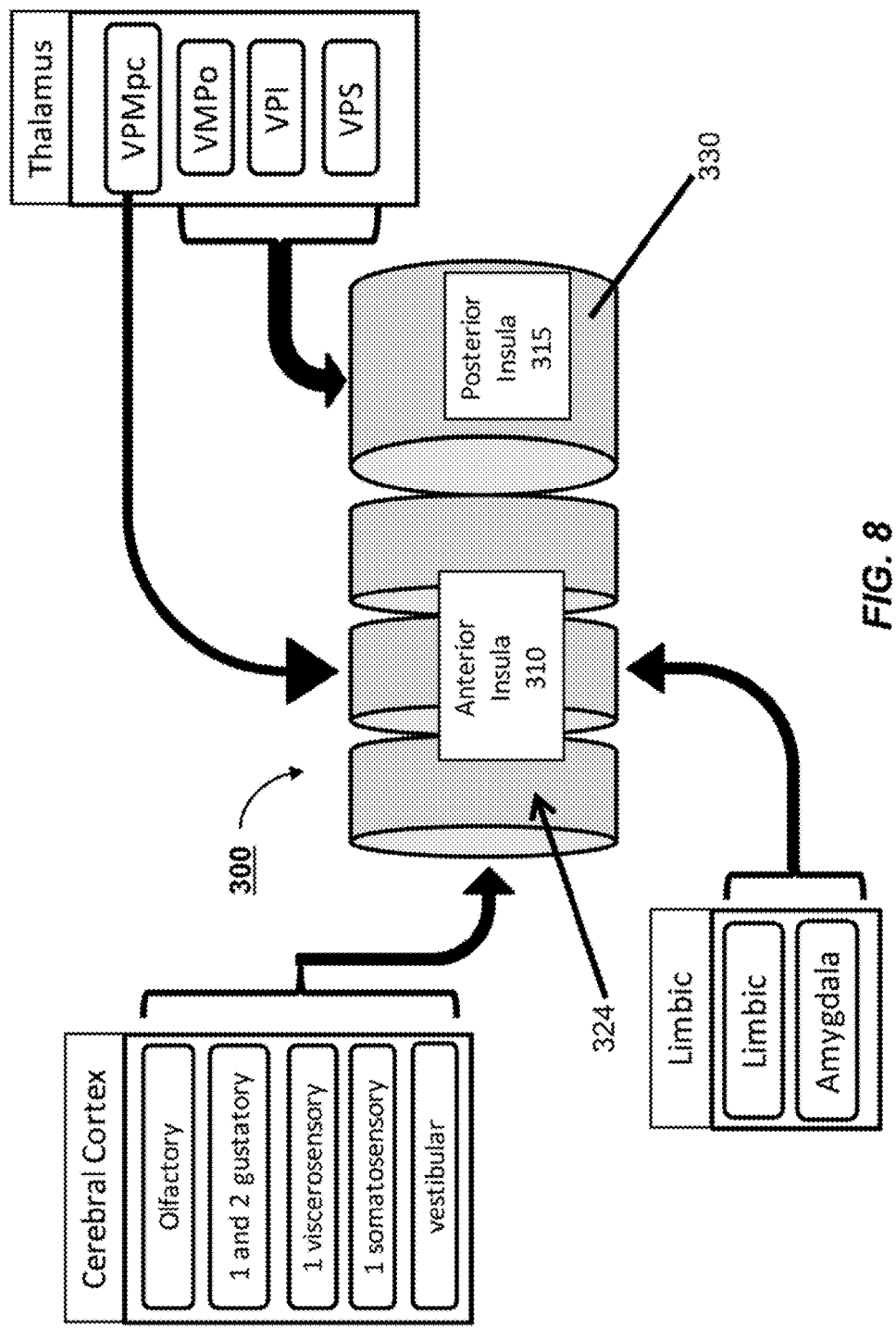
FIG. 8 illustrates a block diagram of the insular cortex.

FIG. 8 illustrates a block diagram of the insular cortex 300. Each subdivision of the insular cortex 300 includes distinct afferent and efferent projections. The insular cortex 300 is divided into two parts: the larger anterior insula 310 and the smaller posterior insula 315. The anterior insula 310 is subdivided by shallow sulci into three or four short gyri 324. The posterior insula 315 is formed by a long gyms 330.The insular cortex 300 receives afferent input from the dorsal thalamus and sensory cortical areas. The insular cortex 300 is reciprocally connected with the amygdala and other limbic and cortical structures. The insular cortex 300 also sends efferent projections to the premotor cortex and ventral striatum, and contains dense local intrainsular connections.

The thalamic nuclei provide a dense source of afferent inputs to the insula 300. The ventral posterior superior (VPS) and the ventral posterior inferior (VPI) thalamic nuclei receive afferents from the vestibular nuclei and project to the parietoinsular vestibular cortex and other cortical areas. The ventromedial posterior (VMPo) thalamic nucleus receives afferent inputs from the lamina spinothalamic neurons that carry nociceptive and thermoreceptive sensory information. The VMPo has efferent projections to the posterosuperior part of the insula 300, which has been designated as the insular nociceptive and thermoreceptive cortex. The parvocellular part of the ventral posteromedial (VPMpc) thalamic nucleus receives projections from the nucleus of the solitary tract. The VPMpc includes the medial and the lateral subdivisions, which have distinct projections. The medial portion of the VPMpc (VPMpc med) receives afferents from the rostral nucleus of the solitary tract, which receives gustatory sensory information, and projects to the granular, anterosuperior insular cortex. The granular, anterosuperior insular cortex represents the primary gustatory cortex. The lateral portion of the VPMpc (VPMpc lat) receives projections from the caudal nucleus of the solitary tract, which is the termination site for sensory visceral information from the cardiovascular and gastrointestinal systems. The region of the insula 300 receiving afferents from the caudal nucleus of the solitary tract is known as the insular viscerosensory cortex.

The insular cortex 300 also receives projections from various cortical areas. The agranular anterior part of the insula forms a part of the orbital network and receives projections from the olfactory prepiriform cortex, primary and secondary gustatory cortices, and the primary viscerosensory insular cortex. The posterosuperior insular cortex includes the insular somatic association cortex, and receives afferents from the primary somatosensory, vestibular cortices, and the auditory association areas.

The anterobasal portion of the insula 300 makes several strong, reciprocal connections with various limbic structures including the entorhinal, perirhinal, posterior orbitofrontal, temporopolar, and cingulate cortices and the amygdala. This region, designated as the insular limbic cortex, is thought to relate events in the external environment to motivational states.

Figure 9A:
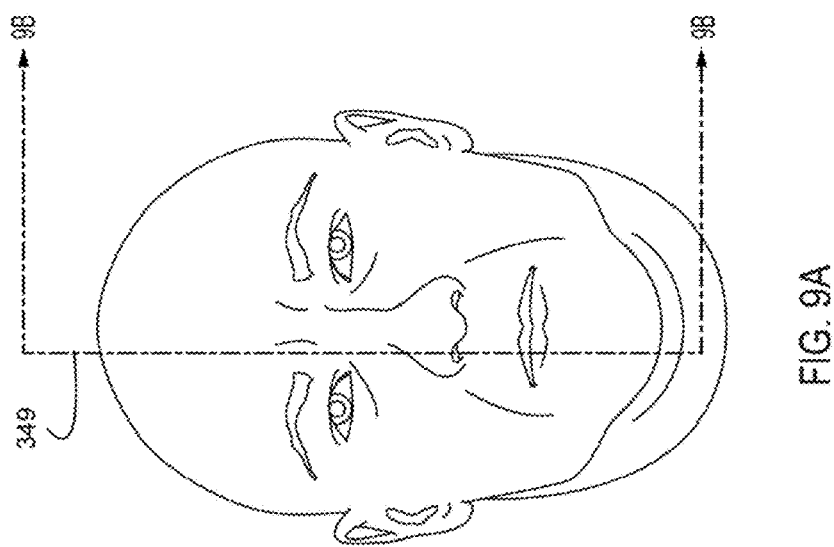
FIG. 9A illustrates the position of a plane of a sagittal section through a patient.

FIG. 9A illustrates the position of a plane 349 of a sagittal section through a patient. FIG. 9B illustrates the sagittal section as an MRI image 350. The MRI image 350 illustrates the relative position of the insula 300 in the patient's brain.

Figure 10B:
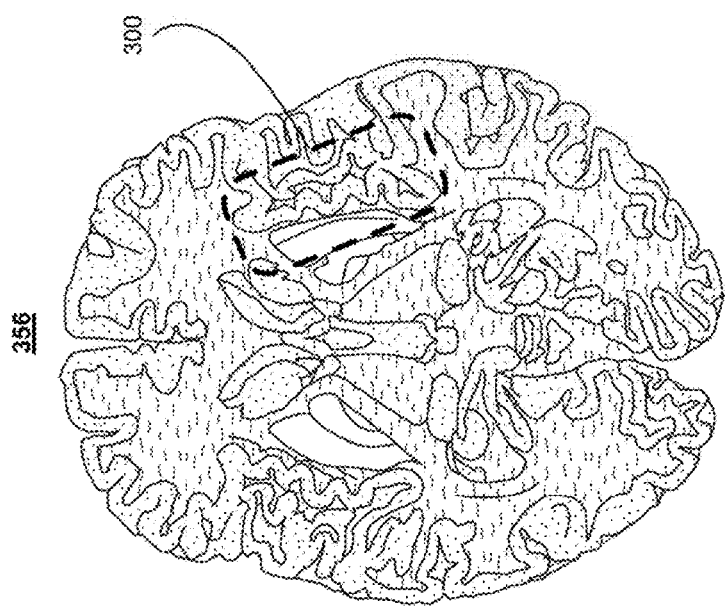
FIG. 10B illustrates an MRI image at the horizontal section illustrated in FIG. 10A.

FIG. 10A illustrates the position of a plane 355 of a horizontal section though a patient. FIG. 10B illustrates the horizontal section as an MRI image 356. The MRI image 356 illustrates the relative position of the insula 300 in a patient's brain.

Figure 11B:
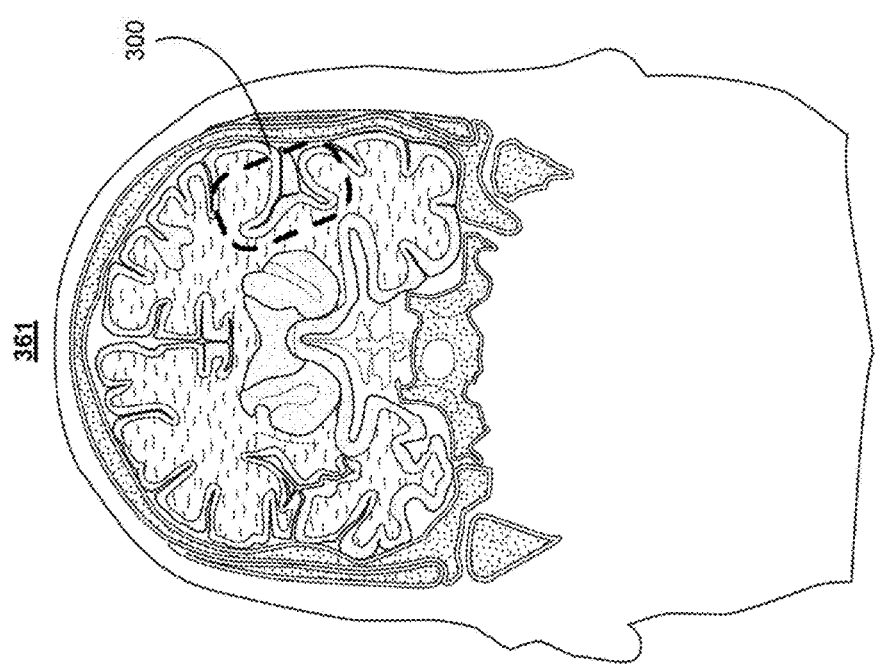
FIG. 11B illustrates an MRI image at the coronal section illustrated in FIG. 11A.

FIG. 11A illustrates the position of a plane 360 of a coronal section though a patient. FIG. 11B illustrates the coronal section as an MRI image 361. The MRI image 361 illustrates the relative position of the insula 300 in a patient's brain.

Figure 12A:
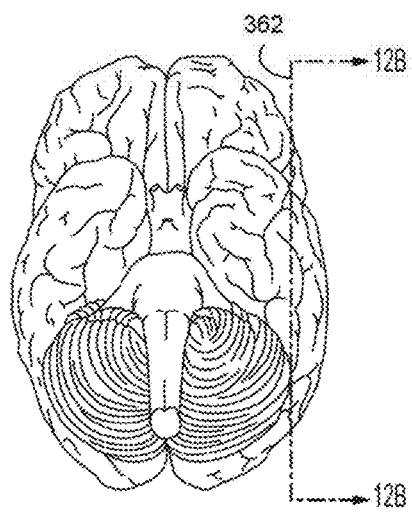
FIG. 12A illustrates the position of a plane of a sagittal section through a patient.
Figure 12B:
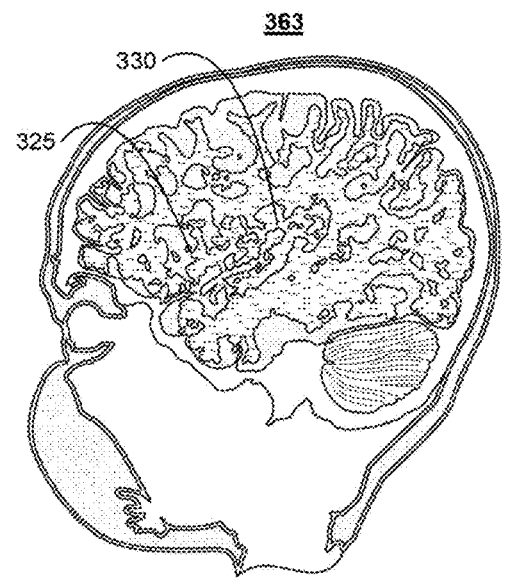
FIG. 12B illustrates a MRI image at the sagittal section illustrated in FIG. 12A.

FIG. 12A illustrate the position of a plane 362 a sagittal section through a patient. FIG. 12B illustrates the sagittal section as an MRI image 363. The MRI image 363 illustrates the long gyms 330 and the short gyri 324.

Function of the Insular Cortex

In the 1950s, the insular cortex 300 was believed to be a vegetative structure, controlling visceral sensation and motor activity. More recent studies have shown that the insular cortex 300 plays a role in at least 20 separate processes that range from basic viscerosensory and visceromotor functions to the awareness of self. The role of the insular cortex 300 in the modulation of these functions are discussed and summarized in Table 1, below. Functional differentiation of the insular cortex in humans is illustrated in FIG. 13.

Figure 13:
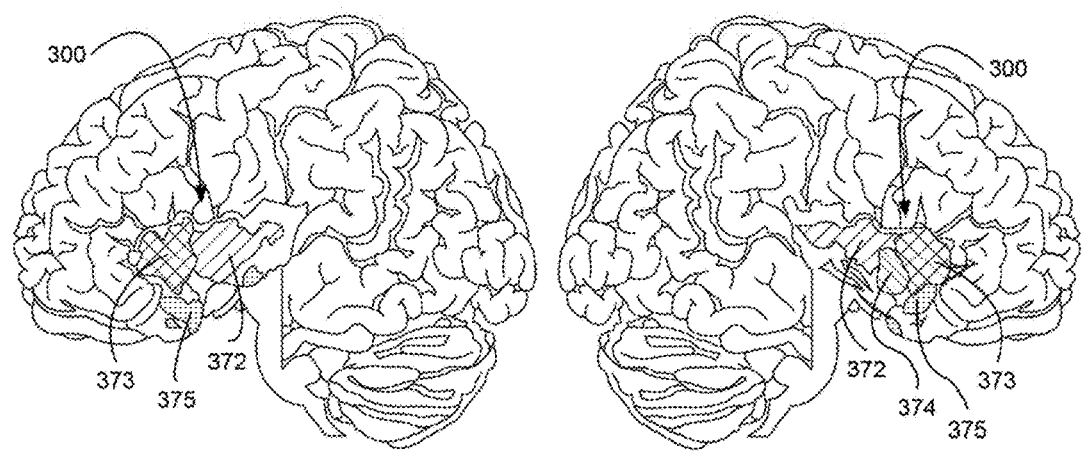
FIG. 13 illustrates an example left insula cortex and an example right insula cortex.

FIG. 13 illustrates the left insula cortex 300 and the right insula cortex 300. A first region 372 of each insular cortex 300 controls sensorimotor function. A second region 373 of each insular cortex 300 controls cognitive function. A third region 374 of each insular cortex 300 controls chemical sensory function. A fourth region 375 of each insular cortex 300 controls social-emotional function.

Since the insular cortex 300 mediates a wide variety of functions, it can be associated with various neurological disorders, including frontotemporal demential, spatial neglect, and with neuropsychiatric disorders, such as schizophrenia, depression, autism, eating disorders, anxiety, Parkinson's disease, and addiction.

One of the functions of the insular cortex 300 is that of awareness of one-self, which includes interoception, or awareness of the physiological state; awareness of external stimuli such as taste and smell, emotions, movement, and the perception of time. Imaging studies have shown that the insular cortex is activated by a variety of interoceptive stimuli, including heart beat, Valsalva manoeuvre, touch, itch, sexual arousal, hot or cold temperatures, and distention of the stomach, rectum or bladder. The insula 300 can be activated by movement, as well as association of movement. Viewing pictures of one's self can activate the right insular cortex, supporting the notion that this region participates in self-recognition. Furthermore, the insular cortex 300 can be activated in response to a variety of emotional feelings, including maternal and romantic love, fear, anger, sadness, happiness, sexual arousal, unfairness, empathy, and trust.

The insular cortex 300 can also be involved in the control of motor functions. The insular cortex 300 can play a role in visceromotor control by affecting the motor component of the autonomic nervous system as well as somatomotor control. Activation of the insular cortex 300 can also be involved in the recovery of motor function following a stroke. The insular cortex 300 can participate in speech coordination, separate from Broca's and Wernicke's areas. Indeed, small lesions caused by ischemic strokes in the anterosuperior insula can cause aphasia. This evidence demonstrates that the insular cortex 300 is a component of the neural circuit that regulates motor control.

In addition to sensory and motor functions, the insular cortex 300 has been implicated in the control of higher cognitive functions. For example, the anterior insular cortex can participate in time perception, in attention, decision making, and goal-directed behaviour. The anterior insular cortex contains a number of specialized, spindle-shaped cells called "von Economo neurons" (VENs) that are found only in more intelligent, social mammals. VENs are believed to participate in complex social cognition, decision-making, and self-awareness. VENs send axons out of the cerebral cortex and may be involved in fast, intuitive decisions required for complex social interaction. Lending support to this concept is the finding that these neurons are dysfunctional in frontotemporal dementia, which is associated with the inability to recognize the emotional impact of behavior on others.

Taken together, this evidence demonstrates that the insular cortex 300 can regulate sensory, motor, and cognitive functions, and connects the emotional states to homeostatic functions. Via connections with cortical regions involved in higher cognitive functions as well as brainstem regions responsible for the transmission of visceral information, the insular cortex 300 can monitor the physiological and external environment and integrates this information to produce appropriate motor and cognitive functions.

TABLE 1

Summary of the functions of the insular cortex.

| FUNCTION | LOCATION IN THE IC | EFFECTS OF DAMAGE | EFFECTS OF STIMULATION |
|---|---|---|---|
| Auditory | Posterior insula | Auditory agnosia | |
| Vestibular | Posterior and anterior, primarily right hemisphere | Vertigo, dizziness, instability | |
| Somatosensory | Posterior | Numbness, dysesthesia, perasthesia | |
| Pain and temperature perception | Dorsal posterior or dorsal mid-insula | Elimination of hot, cold and pain perception | Sensation of pain Sensation of warm and cold temperatures |
| Viscerosensation | Posterior | | Autonomic dysfunction |
| Gustatory sensation | Mid-insula | | Taste sensation |
| Olfaction | Posterocentral, right hemisphere | | Olfactory sensations |

TABLE 1-continued

Summary of the functions of the insular cortex.

| FUNCTION | LOCATION IN THE IC | EFFECTS OF DAMAGE | EFFECTS OF STIMULATION |
|---|---|---|---|
| Visceromotor control | | Cardiac arrhythmias, ECG abnormalities | Vomiting, alterations of the GI tract, respiratory arrest, change in heart rate |
| Somatomotor control | Posterosuperior or posterior | | |
| Speech production | Anterosuperior | Aphasia | Speech arrest; reduce voice intensity |
| Cognitive control | Anterior | | |
| Bodily awareness | Anterior, right hemishpehere | | Denial of paralysis, denial of limbs |
| Self-recognition | Anterior, right hemisphere | | |
| Individual and social emotions | Anterior | | |

Case Studies Illustrating the Connection Between Brain-Infarct and Activities of Inflammatory Reactions In a first case, a man who as a child developed a hemiplegia on the right side at an early age. At the age of 51, he developed severe rheumatoid arthritis only on the non-paretic side.

In a second case, a patient whose spastic paralysis of the right arm persisted after surgical meningioma removal in the left parietal lobe and subsequent radiation. During the course of treatment, the patient developed rheumatoid arthritis, which caused swelling of the left ankle, knee, shoulder, elbow, wrist, and seven joints of the left hand. However, there was no manifestation on the right side of the body. This "protective effect" of hemiplegia has been described not only for rheumatoid arthritis but also for systemic sclerosis.

In a third case, a 60-year old woman who, after a traumatic severing of nerves at digitus 4 of the left hand, showed mutilated joint changes only on the remaining 9 fingers. In this case, underlying, unknown neuroimmunological processes were suspected.

Possible Influence of the Insular Lobe

In one example, immunosuppression after a stroke was influenced not only by the severity of the stroke, but also by its location. To investigate the effect of the location on post-stroke immunosuppression, 384 patients were examined after a brain-infarct of the arteria cerebral media. Patients with an infarct in the insular region, had significantly higher normetanephrine levels, higher concentrations of neutrophil granulocytes, lower levels of eosinophil granulocytes and T-helper lymphocytes compared to patients with infarcts in other regions, despite similar size of the infarct area. Patients with insular infarcts also had more frequent infections in the thoracic cavity. These findings suggest that acute lesions in the area of the insular lobe can cause sympathetic hyper-activation and systemic immunosuppression. These lesions could increase the risk of post-stroke infection. In another study, stimulation of the insular lobe in patients with epilepsy elicited changes in heart rate and blood pressure. Although this study did not examine the effect of insular lobe stimulation on infection rates, the results suggest the possibility that stimulation of the insular lobe affect the cardiovascular as well as the immune system.

As described by individual case studies, stroke can have a favorable influence on autoimmune diseases, including rheumatoid arthritis and scleroderma. Furthermore, these effects of stroke can occur without the presence of motor deficits. These findings suggest that provoked immunosuppression could be utilized for the treatment of various autoimmune and other diseases, including rheumatoid arthritis, psoriasis, psoriasis arthritis, spondyloarthritis, collagenosis, vasculitis, Guillain-Barré-syndrome, Crohn's disease, colitis ulcerosa, IgG4 related disease or diseases with possible inflammation like osteoarthritis, fibromyalgia without triggering side effects that are often observed with pharmaceutical therapies.

A. Psoriasis

Psoriasis is a chronic, relapsing, benign skin disease that is accompanied by increased scaling of the skin. It is assumed that an inflammatory reaction of T-helper cells causes a significant reduction of the cell cycle of the keratinocytes. The keratinocytes, which usually need 1 month to mature and migrate from the basal layer into the corneal layer, do this with psoriasis in only 5 days. The production of the epidermal cells can even be increased up to 30-times.

B. Psoriatic Arthritis

The psoriatic arthritis is a clinically heterogene inflammatory joint disease that is associated with psoriasis from the group of spondyloarthritiden with potential involvement of bones, joints, tendons, tendon insertion, and the spinal column. Histological or immunhistochemical examinations show an infiltration with CD 8 T-cells, macrophages and an increase expression by TNF-alpha.

C. Spondyloarthritis

The group of spondyloarthritiden diseases exhibit certain pathophysiologic and genetic similarities, especially the association with HLA-B27. Immunpathologically, underlying spondyloarthritis is an inflammation in the area of the bone-cartilage-boarder and the enthesial structures. An interaction between the HLA-B27-allele and bacterial antigens due to a subclinical infection or a disturbance of the barrier-function of the intestinal mucosa is assumed to be a cause of spondyloarthritis. However, not only the intestinal flora, but also mechanical stress seems to be pathophysiologically relevant with spondyloarthritis.

D. Collagenosis

Collagenosis is a systemic connective tissue disease where different immunity phenomena appear on connective tissue and vessels that cause rheumatoid symptoms. A role in diagnostics is played by autoantibodies against cell nuclei material (ANA). The cause of collagenosis is still not known. The cause may include hereditary factors, HLA-antigens, hormones, psychological stress, viruses, and sunlight.

E. Vasculitis

Vasculitis is an inflammatory diseases of the blood vessels. It is classified according to size and type of the affected vessels. Vasculitis involves unspecific symptoms, such as fever, a general feeling of sickness, weight loss, night sweat, fatigue, and stress intolerance. Vasculitis also involves specific symptoms, such as inflammation of the nose, sinusitis, exanthema, impairment of the nervous system, ophthalmitis, and the inflammation of the muscles and joints. The cause and pathogenesis of vasculitis, is not known.

F. Guillain-Barré-Syndrome

Guillain-Barré-syndrome is an acute neurological disease with inflammatory changes of the peripheral nervous system. Guillian Barré syndrome affects the nerve roots that emerge from the spinal cord and the associated forward or proximal nerve sections. The myelin sheath, which surrounds the nerve fibres, is attacked and destroyed by the immune system. The exact cause is not known, in some cases, previous infections are held accountable.

G. Morbus Crohn

Crohn's disease is a chronic, granulomatous inflammation of obscure aetiology. Crohn's disease can affect every part of the gastrointestinal tract. There may be a genetic predisposition for this disease. Several hereditary factors were discovered. In at least some Crohn's disease patients, there is a defect of the barrier between the intestinal lumen and the organism. Half of all patients develop intestinal complications, such as strictures or fistulas. Most patients need at least one surgical intervention during their lifetime.

H. Ulcerative Colitis

Ulcerative colitis is a chronic, idiopathic, inflammatory intestinal disorder, marked by clinically variable expressions of disease activity. It exhibits several inflammatory properties, including immune activation, leukocyte infiltration and changes in vessel density. Many of the highly regulated inflammatory cytokines affect the angiogenesis and are released by different cell populations, such as infiltrating immune cells and endothelial cells. Unlike Crohn's disease, mostly the colon is affected by the inflammation, and the inflammation is limited to the mucosa and submucosa.

I. IgG4-Related Diseases

IgG4-related diseases are an increasingly recognized syndrome. With the involvement of different organs, it is accompanied by tumor-like swelling, lymphoplasmacytic infiltrate that is rich in IgG4-positive plasma cells, and increased serum IgG4 concentrations. The diseases have been documented in a variety of organ systems, including pancreas, bile ducts, salivary glands, kidneys, lungs, skin, prostate, and the orbita.

J. Osteoarthritis

Osteoarthritis is a degenerative joint disease that mainly affects weight-bearing joints in the body, especially the hips and knees. Inflammatory processes with both, pro- and anti-inflammatory as well as angioproliferative and chemotactic cytokine is increasingly discussed as an important part of the pathophysiology.

K. Fibromyalgia

Fibromyalgia is characterized by proliferated pain with changing localization within the muscles, around the joints, back pain. Fibromyalgia is also characterized by sensitivity to pressure pain, fatigue; insomnia; morning stiffness; lack of concentration and drive; weather sensitivity; sensation of swollen hands, feet and face; and many more symptoms. The etiology, as well as the pathogenesis, of the disease is unexplained.

L. Marie-Bamberger Syndrome

Secondary hypertrophic osteoarthropathy (HOA), also known as Marie-Bamberger syndrome, is a rare neoplastic syndrome featuring clubbing of the tips of the digits, periosteal proliferation, synovial effusion of adjacent joints, and bronchial carcinoma. This bone changes appears often before the carcinoma. It is unknown why patients develop this carcinoma and why only a few patients develop periosteal proliferation. If hyperactivity of the insular cortex leads to the synovial effusion and possibly to carcinoma, it may be mitigated through insular cortex stimulation as described herein.

X-Ray Findings

Computer tomography (CT) is an imaging technique in radiology. Through computer-based evaluation, a multitude of X-rays are taken of an object from different anglesto generate sectional images. These images can depict the weakening of tissue. Within medical terminology, tissue that exhibits a lower absorption coefficient than expected is called a hypodense (black in a CT image), and tissue with a higher weakening coefficient is called hyperdense (white in a CT image). Bones and similarly dense structures are depicted in white, and air and water are depicted in black. In a CT image of the skull, brain furrows and the ventricular systems are depicted as black, and the skull bones are depicted as white. Healthy brain tissue is depicted as gray.

Figure 14:
FIG. 14 illustrates a cranial computer tomography (CT) image of a female patient who developed a right part-media infarction.

FIG. 14 illustrates a cranial CT image 500 of a female patient who developed a right part-media infarct. The noticeable black structure 501 of the brain tissue is the residuum of the right-hemispherical media infarct along the caudate nucleus, lobus temporalis, and as well as the insular lobe. After the circulatory disturbance, this part of the brain died off, and a scar that is less dense than healthy brain tissue remained.

Magnetic resonance tomography (MRT) (also referred to as magnetic resonance imaging (MRI) generates sectional images of the human body that allow for the assessment of organs and many pathological organ alterations. The examination method uses a physical principle where nuclei with odd numbers of protons or neutrons have an intrinsic angular momentum (e.g. spin). Under normal conditions the spins are disorderly. However, if a strong magnetic field is applied, the spins align like a compass needle in a parallel or anti-parallel manner to the magnetic field direction. The orientation of the nuclear spin alone would not generate an image. Therefore, a short, high frequency impulse is generated vertical to the direction of the magnetic field. After the impulse, the nuclear spins align back towards the outer magnetic field and emit energy in the form of heat to the environment. This process of reorientation, is called a "T1-relaxation." T1-relaxation depends mainly on the thermal conductivity of the tissue. Tissue with fast heat transfer (e.g., fatty tissue) is depicted in T1-weighted images as lighter, and tissue with slower heat transfer is depicted as darker (e.g., liquid).

Figure 15:
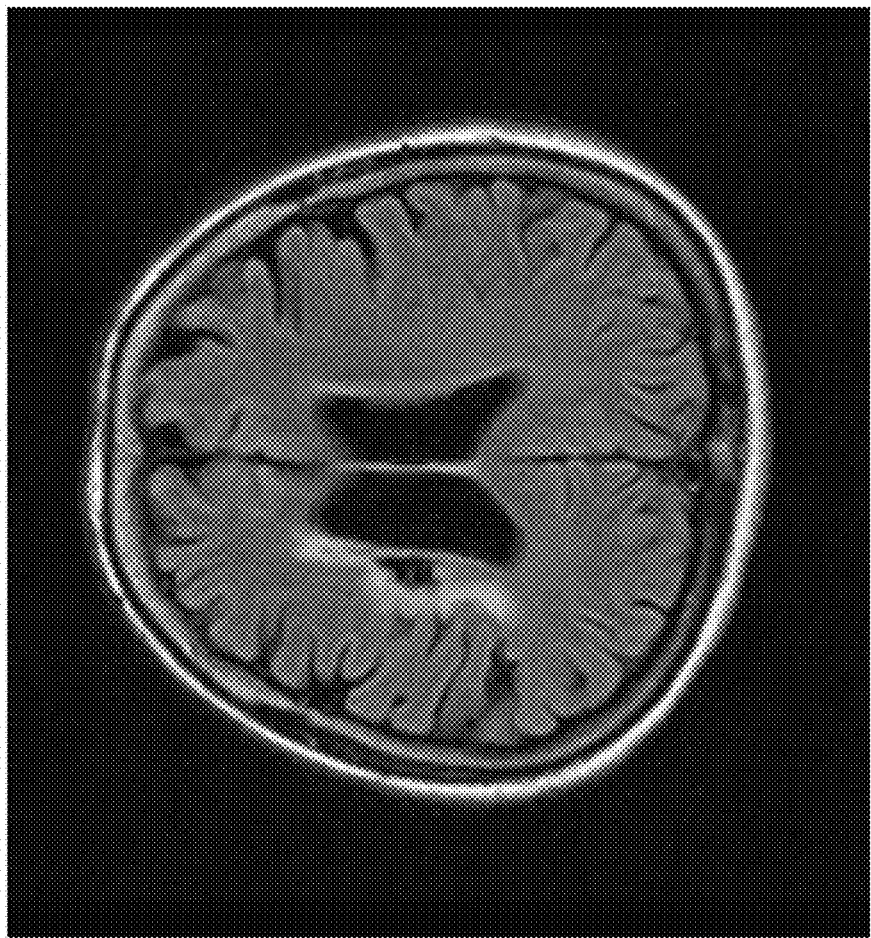
FIG. 15 illustrates the cranial MRI image of the same female patient whose CT image is illustrated in FIG. 14.

FIG. 15 illustrates the cranial MRT image 505 of the same female patient whose CT image 500 is illustrated in FIG. 14. The MRT image 505 was captured roughly 9 months before the capture of the CT image 500. In the TIRM-sequence used here, the old brain infarction is characterized by hyperintensity. It shows residues of an extended, right-sided media infarction with a substance defect of the right insular lobe.

Skeletal scintigraphy is an imaging technique in nuclear medicine that serves to verify parts of bones with a heightened bone metabolism. The physiological principle is based on chemisorption. The $^{99m}$Tc-marked bisphosphonate, such as oxidron acid, accumulates on the bone surface. The extent of the accumulation depends on different factors: regional blood flow, capillary permeability, and the activity of the osteoblasts. Areas with a heightened bone metabolism are depicted darker in the image and may indicate inflammatory alterations such as, rheumatoid arthritis.

Figure 16:
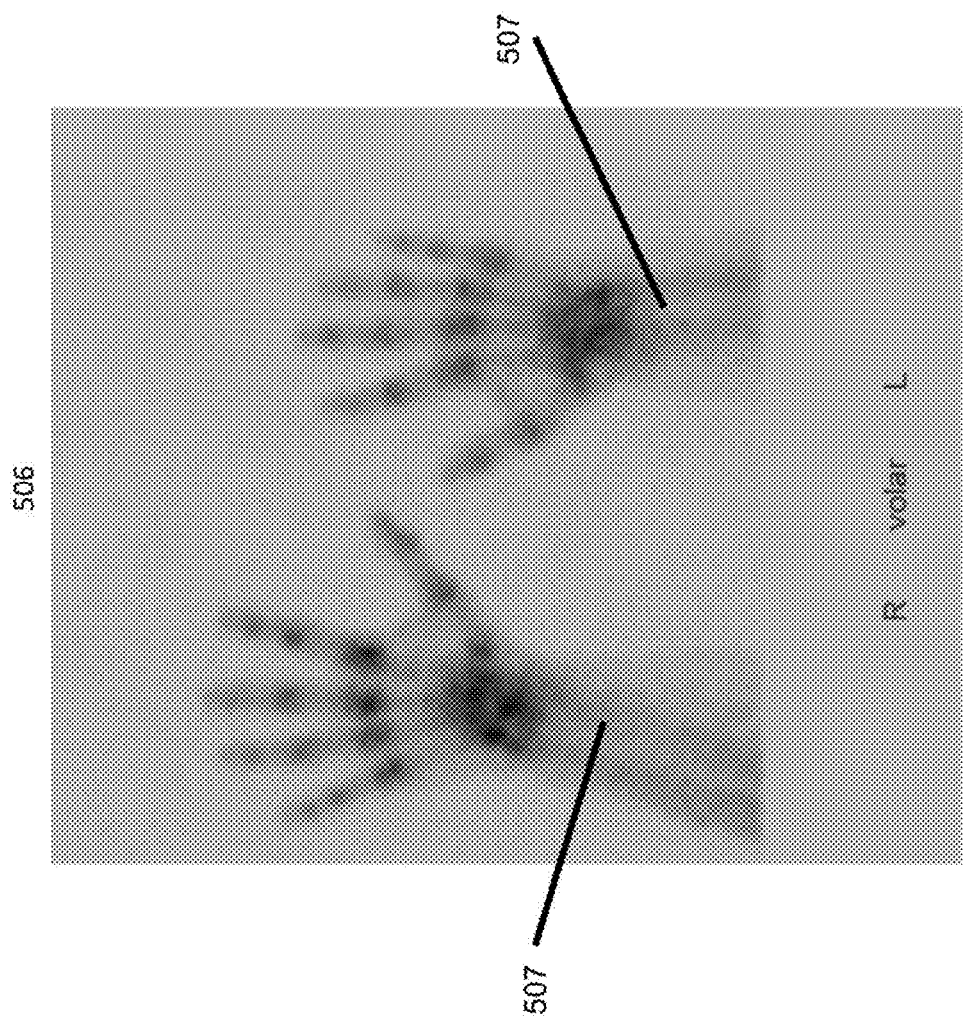
FIG. 16 illustrates a scintigraphy image of the hands of the female patient illustrated in FIG. 14 and FIG. 15.

FIG. 16 illustrates a scintigraphy image 506 of the hands of the female patient illustrated in FIG. 14 and FIG. 15. The scintigraphy image 506 illustrates anuclide distribution at the joints of the hands 507. The image 506 illustrates an emphasis of the metacarpophalangeal joints, right more than left, which are concurrent with rheumatoid arthritis. Collectively, FIGS. 14-16 illustrate that a brain infarction can reduce the intensity of the disease activity of rheumatoid arthritis on the contralateral side. Stimulation of the neurological targets described herein can result in a similar reduction in the intensity of rheumatoid arthritis and the other inflammatory diseases. The electrical stimulation can mimic the inhibition caused by the above described lesions without causing the resulting neurological impairment.

With conventional x-ray imaging, areas of the bodies of patients are x-rayed from one direction. On the opposite side, the radiation is registered with suitable materials and converted into an image. Bones absorb more radiation than soft tissue and therefore project a shadow that appears white on the x-ray. X-ray images of healthy patients show the finger bones in an almost homogenous white tone as an expression of a normal mineralization with a sharp boundary. Indirect signs of rheumatoid arthritis can include a demineralization close to the joint, which can cause the bone near the joint spaces to appear gray, and a swelling of the soft tissue. Direct signs of arthritis can include the narrowing of the joint space, a thinning of the bordering lamella (the bone's edge impresses with weaker intensity), and the erosions (interruption of the bony contours), which appear on x-ray as black holes in the bone.

Figure 18:
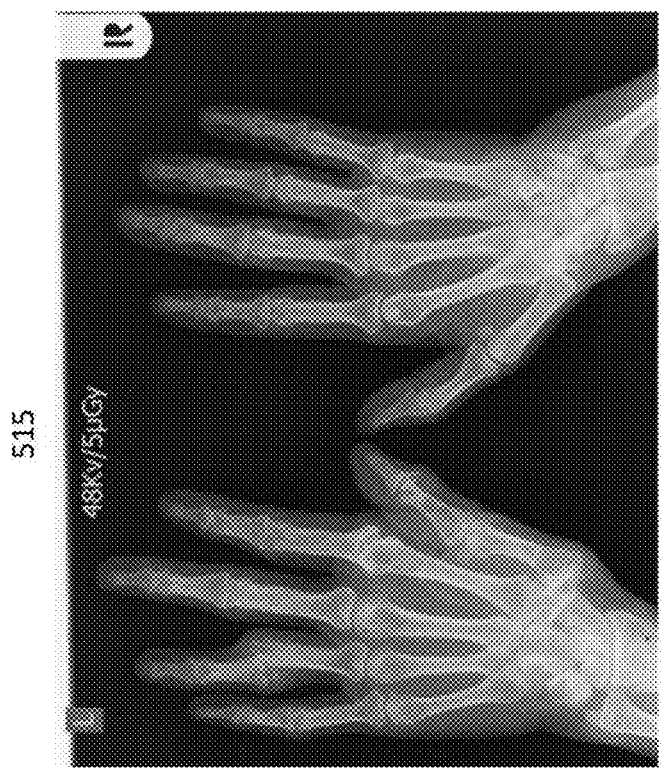
FIGS. 17 and 18 illustrate x-rays of the hands of a 68-year-old female patient, who has a paralysis of the right side since birth.
Figure 17:

FIGS. 17 and 18 illustrate x-rays 510 and 515, respectively, of the hands of a 68-year-old female patient, who has a paralysis of the right side since birth. Twenty-one months passed between the taking of the x-ray 510 and the x-ray 515, in which the rheumatoid arthritis in the left hand led to significantly more erosion and a subluxation of the 4th interphalangeal joint. With rheumatoid arthritis, it is expected that there is a disease progression at both sides of the body. That is missing here—the right hand does not show erosions. This also supports the thesis of protective effects of a paresis with regards to the inflammatory activity of rheumatoid arthritis.

Figure 20:
FIGS. 19-23 illustrate x-ray images of a patient who suffers from symmetrically progressing psoriatic arthritis for the past several years.
Figure 19:
Figure 22:
Figure 21:
Figure 23:
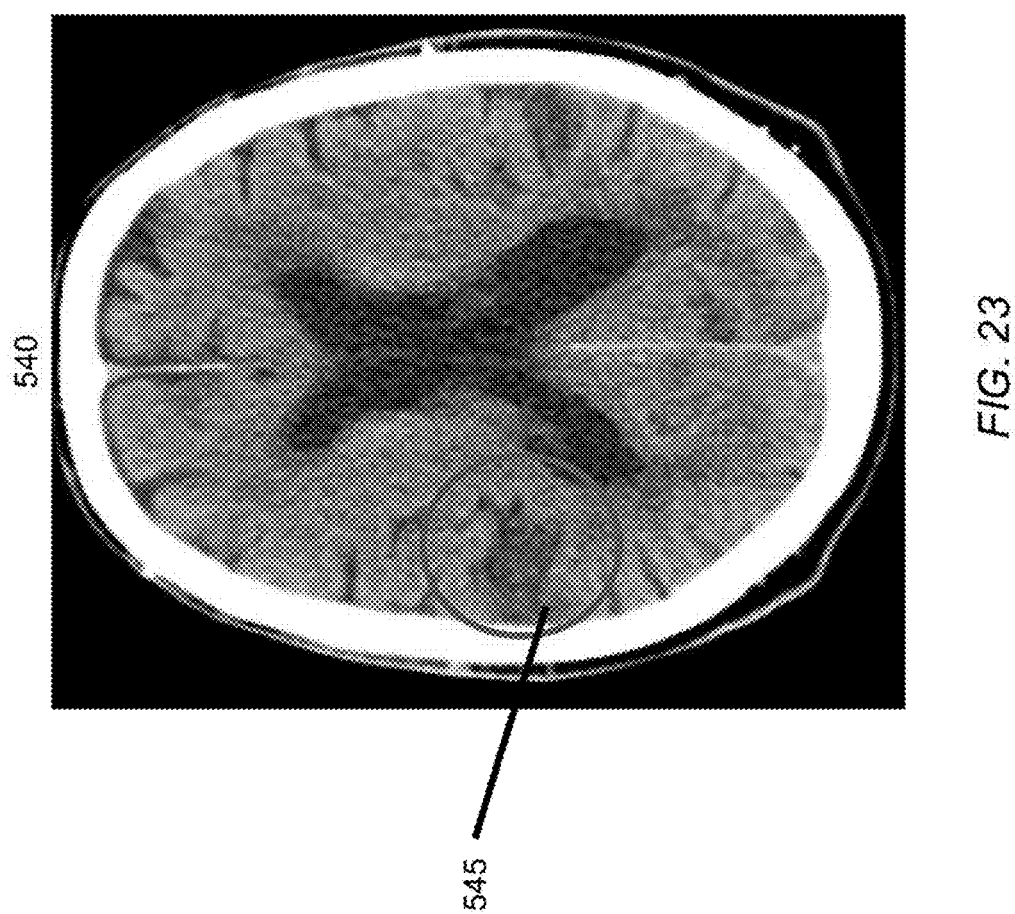

FIGS. 19-23 illustrate x-ray images of a patient who suffers from symmetrically progressing psoriatic arthritis for the past several years. The arthritis presented on the right side with an increasing erosion and narrowing of the joint spaces after an insult of the right side of the brain in 2012, while the increase in erosion and narrowing did not occur on the left side of the patient. FIGS. 19 and 20 illustrate x-rays 520 and 525, respectively, of the feet of the patient. Thirteen months passed between the taking of the x-ray 520 and the x-ray 525, in which the psoriatic arthritis in the right foot led to significantly more erosion. FIGS. 21 and 22 illustrate x-rays 530 and 535, respectively, of the hands of the patient. Thirteen months passed between the taking of the x-ray 530 and the x-ray 535, in which the psoriatic arthritis in the right hand led to significantly more erosion. FIG. 23 illustrates an x-ray 540 illustrating the patient's neurological injury 545.

The Insular Cortex Surgical Targets

The devices described herein are used in the surgical implantation of at least one neurostimulation lead in at least one structure of the insular cortex, in order to reduce the symptoms of autoimmune and other disorders. The devices can reduce the symptoms by stimulating predetermined neurological targets.

The neurostimulation leads described herein can be implanted near the neurological target using a stereotactic implantation device. In some implementations, the surgical navigation can be aided by CT images, MRI images, or both. The target of the neurostimulation lead can be in or near a structure of the insular cortex. The structure of the insular cortex can be any one of the following volumes where the therapeutic effect would be greatest, e.g., the first, second, third, or fourth gyms of the anterior insula, the superior-anterior insula, the inferior-anterior insula, the anterior-anterior or the posterior-anterior insula, the large insular gyms of the posterior insula, the superior-posterior insula, the inferior-posterior insula, the volumes within several centimeters of the insula that project to or from the insula, and other volumes of the insula that are not here mentioned.

As described above the one or more electrodes placed near the target regions of the insula may be cylindrical (e.g. omnidirectional) or segmented (e.g. directional). In both cases, it is attached to an implantable stimulator that delivers electrical stimulation to the chose insular volume. A cylindrical electrode can deliver a quasi-spherical and omnidirectional stimulation signal to the brain volume. A segmented electrode, can deliver a more focused and directional stimulation field to the brain volume. It is believed that using directional stimulation fields may reduce the occurrence of side effects because smaller portions of the brain can be stimulated.

Figure 24:
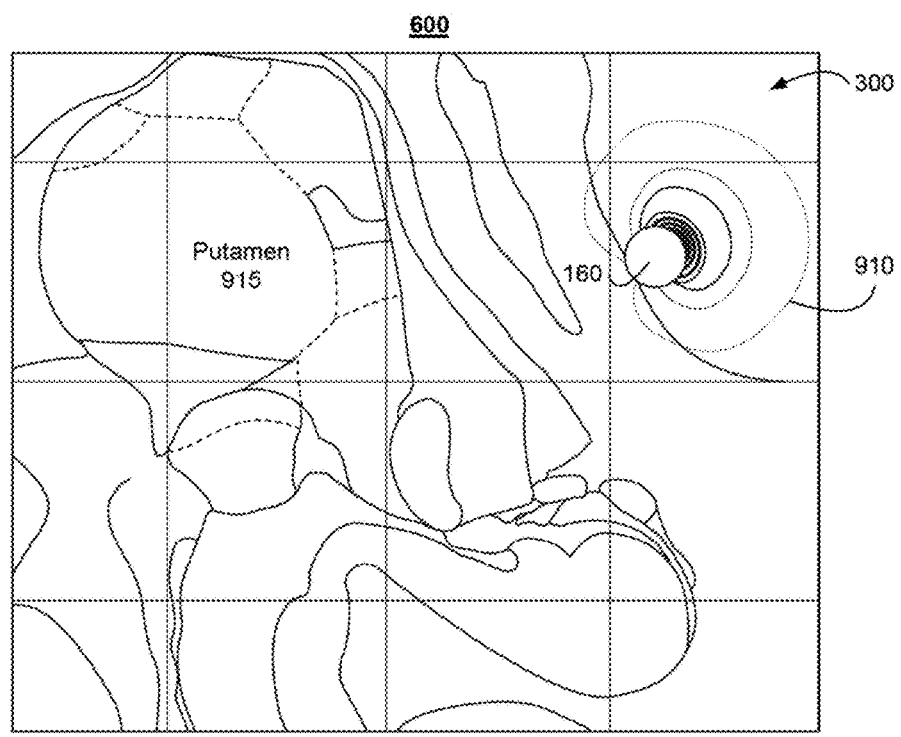
FIGS. 24 and 25 illustrates an example atlas for stereotaxy of the human brain.

FIG. 24 illustrates an example atlas for stereotaxy of the human brain 600. The atlas 600 illustrates the relative placement of an electrode 160. The electrode 160 can be a directional electrode. The directional electrode 160 is placed in plate 29, distance Fp 15,5 of the atlas 600. The directional electrode 160 is placed in the insular cortex 300. A potential field 910 is applied to the tissue from the directional electrode 160. The directional electrode 160 is pointing in a right-upward direction (w/respect to the atlas) for this particular anatomy. Directing the potential field 910 in this direction can reduce side effects because the potential field 910 is directed away from sensitive structures, such as the putamen 915.

Figure 25:
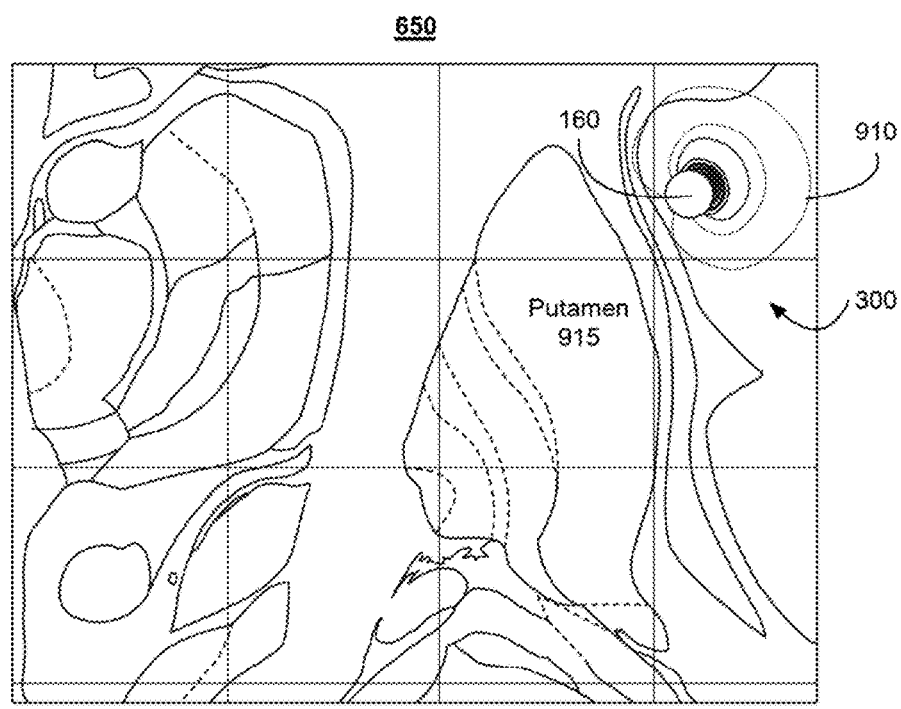

FIG. 25 illustrates an example atlas for stereotaxy of the human brain 650. The atlas 650 illustrates the relative placement of an electrode 160. The electrode 160 can be a directional electrode. The directional electrode 160 is placed in plate 27, distance Fp 3,0 of the atlas 650. The directional electrode 160 is placed in the insular cortex 300, from which a potential field 910 is applied to the tissue from the directional electrode 160. The electrode 160 is pointing in a right-upward direction (with respect to the atlas) for this particular anatomy. The directional electrode 160 can direct the potential field 910 away from sensitive structures such as the putamen 915, which can reduce side effects.

Various implementations of the microelectrode device have been described herein. These embodiments are giving by way of example and not to limit the scope of the present disclosure. The various features of the embodiments that have been described may be combined in various ways to produce numerous additional embodiments. Moreover, while various materials, dimensions, shapes, implantation locations, etc. have been described for use with disclosed embodiments, others besides those disclosed may be utilized without exceeding the scope of the disclosure.

Devices described herein as either acute or chronic may be used acutely or chronically. They may be implanted for such periods, such as during a surgery, and then removed. They may be implanted for extended periods, or indefinitely. Any devices described herein as being chronic may also be used acutely.

The present disclosure is not to be limited in terms of the particular embodiments described in this application, which are intended as illustrations of various aspects. Modifications and variations can be made without departing from its spirit and scope of this disclosure. Functionally equivalent methods and apparatuses may exist within the scope of this disclosure. Such modifications and variations are intended to fall within the scope of the appended claims. The subject matter of the present disclosure includes the full scope of equivalents to which it is entitled. This disclosure is not limited to particular methods, reagents, compounds compositions or biological systems, which can vary. The terminology used herein is for the purpose of describing particular embodiments, and is not intended to be limiting.

With respect to the use of substantially any plural or singular terms herein, the plural can include the singular or the singular can include the plural as is appropriate to the context or application.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Claims directed toward the described subject matter may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, such recitation can mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction would include but not be limited to systems that have A alone, B alone, C alone, A and B together, A and C together, B and C together, and/or A, B, and C together, etc.). Any disjunctive word or phrase presenting two or more alternative terms, whether in the description, claims, or drawings, can contemplate the possibilities of including one of the terms, either of the terms, or both terms. For example, the phrase "A or B" includes the possibilities of "A" or "B" or "A and B."

Terms of degree such as "about" or "substantially" include the identified numbers and a range of +/−10% from the identified number. References to "or" include both exclusive or and inclusive or examples.

In addition, where features or aspects of the disclosure are described in terms of Markush groups, the disclosure is also described in terms of any individual member or subgroup of members of the Markush group.

Any ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. Language such as "up to," "at least," "greater than," "less than," and the like include the number recited and refer to ranges which can be subsequently broken down into subranges as discussed above. Finally, a range includes each individual member.

One or more or any part thereof of the techniques described herein can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program can be stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis, preprocessing, and other methods described herein can also be implemented as a computer-readable storage medium, configured with a computer program, where the storage medium so configured causes a computer to operate in a specific and predefined manner to perform the functions described herein. In some embodiments, the computer readable media is tangible and substantially non-transitory in nature, e.g., such that the recorded information is recorded in a form other than solely as a propagating signal.

In some embodiments, a program product may include a signal bearing medium. The signal bearing medium may include one or more instructions that, when executed by, for example, a processor, may provide the functionality described above. In some implementations, signal bearing medium may encompass a computer-readable medium, such as, but not limited to, a hard disk drive, a Compact Disc (CD), a Digital Video Disk (DVD), a digital tape, memory, etc. In some implementations, the signal bearing medium may encompass a recordable medium, such as, but not limited to, memory, read/write (R/W) CDs, R/W DVDs, etc. In some implementations, signal bearing medium may encompass a communications medium such as, but not limited to, a digital or an analog communication medium (e.g., a fiber optic cable, a waveguide, a wired communications link, a wireless communication link, etc.). Thus, for example, the program product may be conveyed by an RF signal bearing medium, where the signal bearing medium is conveyed by a wireless communications medium (e.g., a wireless communications medium conforming with the IEEE 802.11 standard).

Any of the signals and signal processing techniques may be digital or analog in nature, or combinations thereof.

While certain embodiments of this disclosure have been particularly shown and described with references to preferred embodiments thereof, various changes in form and details may be made therein without departing from the scope of the disclosure.

What is claimed:

1. A method for treating an autoimmune disorder, the method comprising:
    implanting an implantable stimulator into a patient;
    implanting a lead into the patient, the lead having a MEMS film comprising:
        a plurality of electrodes;
        a plurality of periphery traces at least partially encircling each of the plurality of electrodes; and
        at least two connection points coupling each of the plurality of periphery traces with a respective one of the plurality of electrodes;
    driving the lead toward a first target location in the patient, wherein the first target location comprises one of a first, a second, a third, or a fourth gyms of an anterior insular cortex; a superior-anterior insula; an inferior-anterior insula; an anterior-anterior insula; a posterior-anterior insula; a large insular gyms of a posterior insula; a superior-posterior insula; or an inferior-posterior insula;
    generating, by the implantable stimulator, an electrical signal; and
    delivering the electrical signal to the first target location via at least one of the plurality of electrodes.

2. The method of claim 1, further comprising:
    treating an autoimmune disorder with the electrical signal, the autoimmune disorder comprising at least one of rheumatoid arthritis; psoriasis; psoriatic arthritis; spondyloarthritis; collagenosis; vasculitis; guillain-barré syndrome; morbus chrohn; ulcerative colitis; igg4-related disease; osteoarthritis; fibromyalgia; and Marie-Bamberger syndrome.

3. The method of claim 1, further comprising:
    driving a second lead toward a second target location located on a contralateral side of the patient with respect to the first target location.

4. The method of claim 1, wherein at least one of the plurality of electrodes is a directional electrode.

5. The method of claim 4, further comprising:
    recording neurological activity from the target location; and
    selecting a portion of the plurality of electrodes to deliver the electrical signal based on the recorded neurological activity.

6. The method of claim 1, further comprising:
    detecting a presence of an autoimmune disorder symptom; and
    increasing a characteristic of the electrical signal.

7. The method of claim 6, wherein the characteristic of the electrical signal is at least one of an amplitude, a frequency, and a pulse width.

8. The method of claim 1, further comprising:
    detecting a presence of a side effect caused at least partially by the electrical signal; and
    decreasing a characteristic of the electrical signal.

9. The method of claim 1, further comprising:
    determining neurological activity of the target area is below a predetermined threshold; and
    applying the electrical stimulation with a frequency between about 120 Hz and about 140 Hz.

10. The method of claim 1, further comprising:
    determining neurological activity of the target area is above a predetermined threshold; and
    applying the electrical stimulation with a frequency between about 40 Hz and about 60 Hz.

11. The method of claim 1, wherein at least one of the plurality of electrodes is an omnidirectional electrode.

12. The method of claim 11, wherein the omnidirectional electrode is a recording electrode.

13. The method of claim 1, wherein the MEMS film comprises:
    a ribbon cable extending form a distal end of the MEMS film and into a lumen defined by the MEMS film.

14. The method of claim 13, wherein the ribbon cable comprises a plurality of contact pads, wherein each of the plurality of periphery traces are coupled to one of the plurality of contact pads.

15. The method of claim 1, wherein each of the plurality of electrodes comprise a second metal layer.

16. The method of claim 15, wherein the second metal layer comprises at least one of platinum, iridium oxide, or titanium.

17. The method of claim 1, further comprising:
generating the electrical signal with a frequency between about 2 Hz and about 500 Hz.

18. The method of claim 1, further comprising:
generating the electrical signal with a pulse width between about 10 µs and about 500 µs.

19. The method of claim 1, further comprising:
generating the electrical signal with a current between about 0.1 mA and about 12 mA.

20. The method of claim 1, further comprising:
selecting a different one of the at least one of the plurality of electrodes for delivering the electrical signal; and
delivering the electrical signal to the first target location via the different one of the at least one of the plurality of electrodes.

\* \* \* \* \*